(12) United States Patent
Holm-Kennedy

(10) Patent No.: US 7,291,496 B2
(45) Date of Patent: Nov. 6, 2007

(54) ULTRASENSITIVE BIOCHEMICAL SENSOR

(75) Inventor: James W. Holm-Kennedy, Honolulu, HI (US)

(73) Assignee: University of Hawaii, Honolulu, HI (US)

( * ) Notice: Subject to any disclaimer, the term of this patent is extended or adjusted under 35 U.S.C. 154(b) by 534 days.

(21) Appl. No.: 10/854,753

(22) Filed: May 24, 2004

(65) Prior Publication Data

US 2005/0014178 A1 Jan. 20, 2005

Related U.S. Application Data

(60) Provisional application No. 60/473,202, filed on May 22, 2003, provisional application No. 60/516,485, filed on Oct. 31, 2003.

(51) Int. Cl.
*G01N 33/551* (2006.01)

(52) U.S. Cl. ............... 435/287.2; 422/82.01; 422/82.02; 435/6; 435/288.7; 436/514; 436/518; 436/524; 436/527; 436/149; 436/806; 204/403; 204/406; 204/414; 204/420

(58) Field of Classification Search ............. None
See application file for complete search history.

(56) References Cited

U.S. PATENT DOCUMENTS

| | | |
|---|---|---|
| 4,885,623 A | 12/1989 | Holm-Kennedy et al. |
| 4,916,505 A | 4/1990 | Holm-Kennedy |
| 4,926,682 A | 5/1990 | Holm-Kennedy et al. |
| 4,926,693 A | 5/1990 | Holm-Kennedy et al. |
| 4,951,510 A | 8/1990 | Holm-Kennedy et al. |
| 4,960,177 A | 10/1990 | Holm-Kennedy et al. |
| 5,036,286 A | 7/1991 | Holm-Kennedy et al. |
| 5,083,466 A | 1/1992 | Holm-Kennedy et al. |
| 5,095,762 A | 3/1992 | Holm-Kennedy et al. |
| 5,101,669 A | 4/1992 | Holm-Kennedy et al. |
| 5,140,393 A | 8/1992 | Hijikihigawa et al. |
| 5,466,348 A | 11/1995 | Holm-Kennedy |
| 5,784,507 A | 7/1998 | Holm-Kennedy et al. |

FOREIGN PATENT DOCUMENTS

| | | |
|---|---|---|
| JP | 55-010546 A | 1/1980 |
| JP | 08-313476 A | 11/1996 |
| WO | WO 01/64945 A2 | 9/2001 |

*Primary Examiner*—Christopher L. Chin
(74) *Attorney, Agent, or Firm*—James Creighton Wray; Clifford D. Hyra

(57) ABSTRACT

An electronic sensor is provided for detecting the presence of one or more analytes of interest in a sample. The sensor preferably comprises a field effect transistor in which conductance is enhanced by analyte binding to receptors in the active region. An array of sensors may be formed to analyze a sample for multiple analytes.

37 Claims, 25 Drawing Sheets

| Symbol | Description |
|---|---|
| Y | = Receptor to target #1 |
| ⊥ | = Receptor to target #2 |
| Y' | = Receptor to target #3 |
| W | = Receptor to target #4 |
| U | = Receptor to target #5 |
| ξ | = Receptor to target #6 |
| ■ | = Target antigen or chemical |

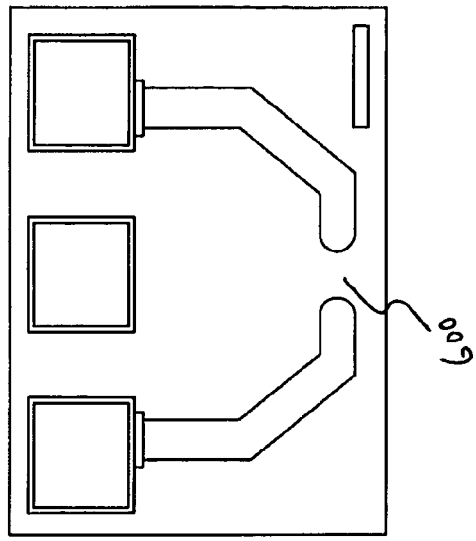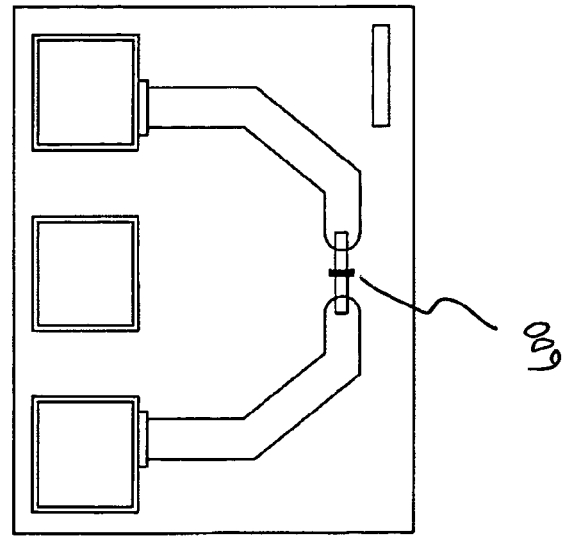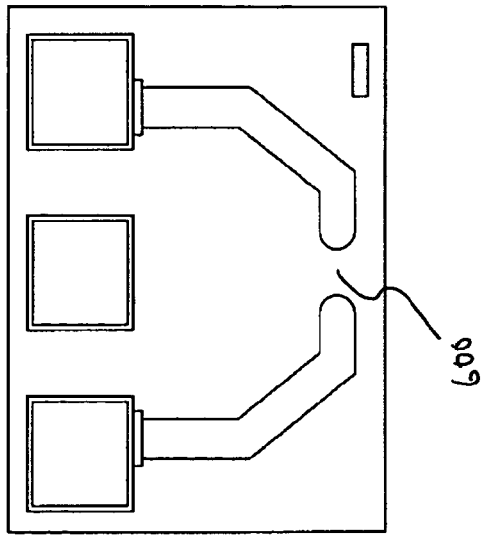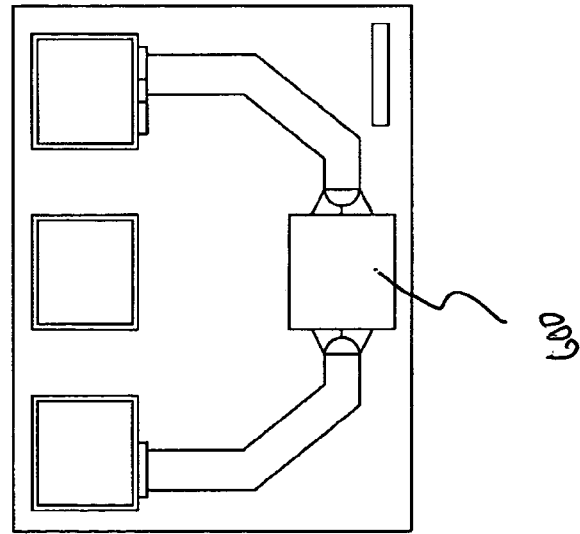
FIG. 10

ULTRASENSITIVE BIOCHEMICAL SENSOR

REFERENCE TO RELATED APPLICATIONS

The present claims priority under 35 U.S.C. §119(e) to U.S. Provisional Application Nos. 60/473,202, filed May 22, 2003 and 60/516,485, filed Oct. 31, 2003.

FIELD OF THE INVENTION

The present invention relates to a sensor for the detection of analytes in a sample. In particular it relates to sensors comprising integrated circuits that can detect the binding of one or more analytes of interest to receptors on the active region of the sensor surface.

BACKGROUND OF THE INVENTION

The identification of analytes of interest in a sample has a wide variety of applications in many fields. For example, in medical diagnostics it is desirable to be able to screen bodily fluids, such as blood, for the presence of particular analytes that may be indicative of a disease or disorder. In other areas, such as bioterror and environmental remediation, it is important to be able to identify the presence of toxic compounds or infectious agents in the environment.

Sensors for identifying analytes of interest may be based on transistors used in integrated circuits. One such sensor is described in U.S. Pat. No. 5,466,348, which is incorporated by reference herein in its entirety.

SUMMARY OF THE INVENTION

In one aspect of the present invention a sensor is provided for detecting the presence of an analyte of interest in a sample. The sensor may be used, for example, to detect the presence of toxins, pathogens, disease markers, nucleic acids, proteins or other molecules or complexes in a sample.

The sensor preferably comprises a receptor for the analyte of interest bound to the active region of a field effect transistor (FET). The active region, in turn, overlies a conducting p+ channel connecting a source and drain region. Thus, the sensor typically operates in enhancement mode upon binding of a negatively charged analyte. The sensitivity of the sensor may be increased by applying a bias to a back gate.

In some embodiments, the active region comprises a gate electrode, such as a polysilicon gate, over a gate dielectric layer. In other embodiments, a gate electrode is not present and the receptor is bound to the dielectric layer, for example a silicon nitride layer.

The receptor is preferably selected from the group consisting of antibodies, antibody fragments, peptides, oligonucleotides, DNA, RNA, aptamers and organic molecules. In one embodiment, the receptor is bound to the active region via a linker molecule.

In another aspect, a method for identifying the presence of one or more analytes in a sample is provided. The active region of a sensor is contacted with the sample and sensor output is measured. The presence of an analyte of interest in the sample is identified where the sensor output indicates a change in the conductance of the channel upon contacting the sample. The sensor output is preferably a measure of conductance, voltage or resistance. The change of conductance resulting from analyte binding may be enhanced by contacting the bound analyte with a secondary charged molecule. A secondary charged molecule may be, for example, an antibody or a bead.

Preferably, the sensor comprises one or more receptors for the analyte of interest bound to the active region. The active region overlies a p+ conducting channel connecting a source and drain region. The source and drain region are typically n− doped.

According to another aspect of the invention, a sensor is provided for detecting the presence of an analyte in the sample, where the sensor comprises a field effect transistor operating in enhancement mode. Binding of the analyte of interest to receptors on the active region of the sensor increases conduction through a channel connecting a source and drain region. In one embodiment the channel is a p+ conducting channel and the analyte is negatively charged. In another embodiment the channel is an n− conducting channel and the analyte is positively charged. In a further embodiment, conduction is increased by the enhancement of a conducting inversion layer in the channel.

The sensors may be arranged to form an array for detecting the presence of one or more analytes in a sample. In one embodiment the array comprises two or more sensors for detecting multiple different toxins in a sample. In another embodiment the array comprises two or more sensors for detecting the multiple disease markers in a sample.

The arrays may comprise multiple sensors with the same type of receptors or sensors with orthogonal receptors for confirming the presence of a particular analyte. In one embodiment the array comprises a first sensor for detecting the presence of a first analyte of interest and a second sensor for detecting the presence of a second analyte. In one embodiment, the first and second analytes are related and the presence of the second analyte provides confirmation of the presence of the first analyte.

BRIEF DESCRIPTION OF THE DRAWINGS

FIG. 10 provides a top view representation of a possible sensor layout. A top view of four different sensors with different geometrical features is shown. The active sensor regions are in the lower central portion of each quad. An array here would constitute an array of either component members of the chip shown, or an array of the group shown, thereby comprising an array of groups of sensors. Such sensor group array components may comprise sensor configurations which vary according to the sensor objectives, sensitivity issues, receptor binding issues or other desirable features.

DETAILED DESCRIPTION OF THE PREFERRED EMBODIMENT

The present invention provides an electronic sensor for detecting analytes in a sample. The sensor comprises one or more receptors that are specific for the analytes of interest attached to a sensing platform. The sensing platform is preferably a semiconductor based transistor which produces an electrical signal in response to analyte binding. As discussed further below, the sensor is compatible with a wide spectrum of targets and allows for the simultaneous detection of multiple analytes. In preferred embodiments, multiple sensors are arranged to form a sensor array.

"Analyte" and "target" refer to a specific material, the presence, absence, or amount of which is to be detected, and that is capable of interacting with a receptor. The analytes that may be detected include, without limitation, molecules, compounds, complexes, nucleic acids, proteins, viruses, bacteria, cells and tissues. As a result, the methods disclosed herein are broadly applicable to many different fields including medical diagnostics, proteomics, genomics, public health, environmental monitoring, drug testing, biodefense, automated testing and telemedicine. Exemplary analytes include, without limitation, biochemical weapons such as anthrax, botulinum toxin, and ricin, environmental toxins, insecticides, aerosol agents, proteins such as enzymes, peptides, nucleic acids such as DNA, RNA and oligonucleotides, pathogens such as viruses and bacteria, blood components, drugs, etc. The target may be naturally occurring or synthetic. One of skill in the art will be able to readily adapt the methods to the particular needs of a specific field.

"Substrate" when used herein refers to the underlying material of the array on which the sensors are formed. Typically the substrate is a solid support and has a rigid or surface. In a preferred embodiment, the substrate is a semiconductor wafer, preferably a silicon wafer. The individual sensors are formed on and/or in the substrate in the desired pattern. The receptors are then attached to the active region of each sensor.

The "active region" of the sensor is the region to which the receptors are attached and in which a signal is detected in response to the binding of an analyte. The "active region" is not to be confused with the "active area," or doped well in which a transistor is defined. Typically, the active region of the sensor is the top gate region of a transistor. However, in some embodiments the active region comprises the gate dielectric over the channel region, such that the receptor becomes the gate after binding.

"Receptor" refers to any molecule that is capable of interacting with a target molecule. Receptors can be, for example and without limitation, antibodies, antibody fragments, peptides, nucleic acids such as oligonucleotides, aptamers, DNA, and RNA, organic molecules, and polypeptides.

The Sensor

Figure 1:
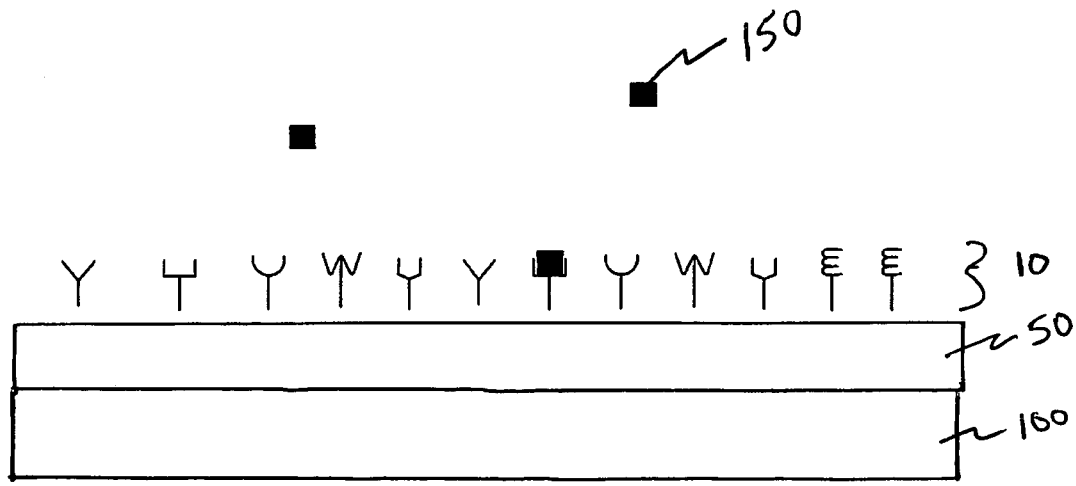
FIG. 1 is a schematic illustration of a sensor incorporating an assortment of different receptors groups. Here the receptors are attached to the active region of a sensor as shown. Each type of receptor provides specific binding to a specific target molecule. If any of the target molecules are present, binding results in a sensor output signal (signature). In this example, the number of receptors specific to each target is assumed to be equal in surface density (receptor number/square micron).

As illustrated in FIG. 1, the sensor comprises one or more receptors 10 attached to an active region 50 which is formed on an underlying solid support 100. Each receptor is specific for an analyte of interest. The sensor is contacted with a sample and if the analyte of interest is present, binding of the analyte 150 to a receptor 10 results in a sensor output signal. The type and magnitude of the signal will depend, in part, upon the charge associate with the analyte.

In some embodiments the sensor comprises more than one type of receptor 10. Each type of receptor 10 is specific for a particular analyte. Multiple copies of each type of receptor 10 are preferably attached to the active region 50 in order to produce a detectable signal upon binding. The number of receptors 10 necessary to produce a detectable signal will depend upon the nature of the analyte and can be readily determined by the skilled artisan.

Thus, the density of receptors 10 on the active area 50 is adjusted in order to produce a detectable signal if an analyte of interest is present in the sample. In addition, the density and absolute number of receptors 10 on each sensor may be adjusted in order to provide additional information about the type and number of analytes 150 present in a sample. For example, as described below, if approximately equal numbers of two or more types of receptor are present, it is possible to determine both the presence and identity of one or more of the corresponding analytes in the sample. On the other hand, the number of receptors 10 of each type can be adjusted such that the sensor can identify the number of analytes 150 present.

Figure 2:
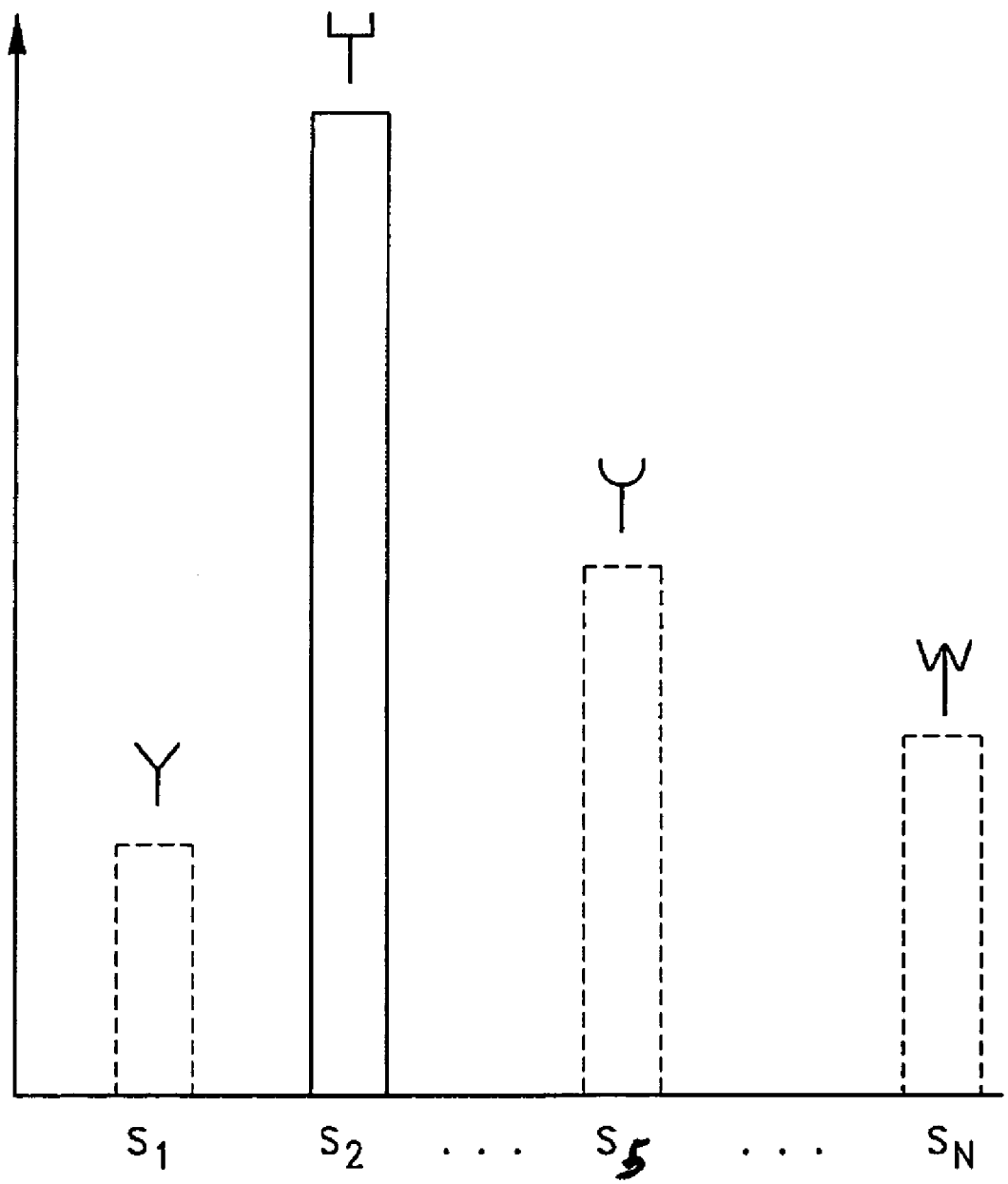
FIG. 2 is a bar chart showing the sensor output signal upon analyte binding to the sensor illustrated in FIG. 1. A sensor signal for each binding target, is schematically represented. The dotted lines indicate what the signal output $S_1$ through $S_N$ would be for receptors groups $R_1$ through $R_N$ if these receptors were fully bound by the specific corresponding antigen. The solid line represents the signal from the sensor for the second receptor ($R_2$). The different signal magnitudes arise from different receptor and target properties such as magnitude of charge and/or chemical potential associated with the bound target biochemical.

In a particular embodiment, the total number of each type of receptor on a given sensor is approximately equal. That is, the number of receptors specific for each analyte is approximately equal. In addition the number of receptors for each analyte type is preferably high enough to produce a detectable signal but low enough that the receptors are readily saturated by a sample containing that analyte type. The magnitude of the output signal produced by binding of each analyte will depend on the receptor and target analyte properties, including the charge and/or the chemical potential associated with the bound analyte. Because of the equal density of each type of receptor, differences in the amplitude of the measured signal are attributable to the identity of the analyte and not to differences in the number of receptor molecules bound. The type of signal expected for each analyte can be predetermined by exposing the sensor to one analyte at a time in a calibration process. As a result, the distinct signal produced by binding of each analyte allows for the determination of the identity of a particular analyte in the sample (FIG. 2). In addition, if more than one analyte is present, the combined output signal is parsed to determine the identity of more than one analyte.

Figure 3:
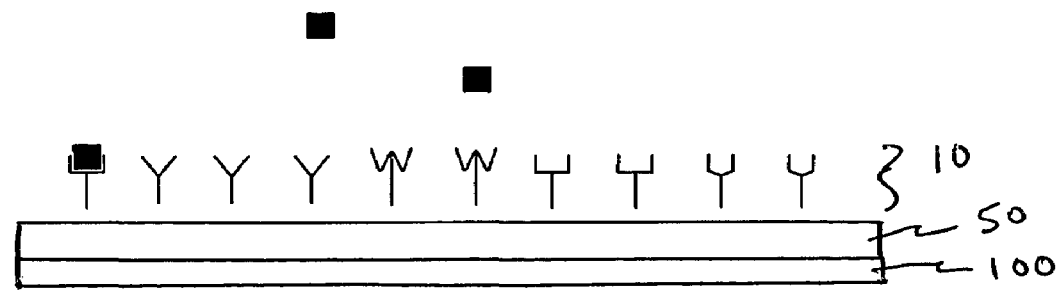
FIG. 3 schematically illustrates a sensor with adjusted receptor densities. A sensor surface overlaying an active sensor region is shown. Different groups of receptors specific to different diseases, and with corresponding different surface densities, are attached to the chemically active surface. The receptor densities for each target are chosen such that the resultant signal for binding to any of the receptor sets is of approximately the same magnitude regardless of which target is present in the sample, as indicated by the bar heights in FIG. 4.
Figure 4:
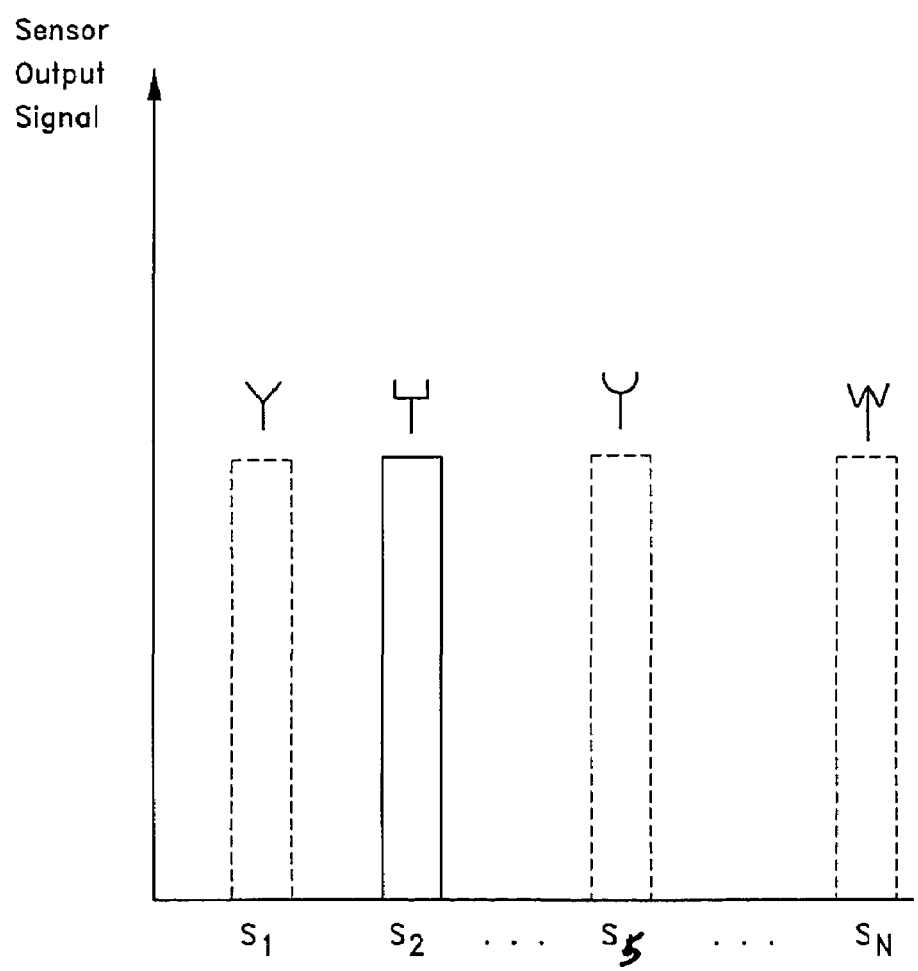
FIG. 4 is a bar graph illustrating the sensor signal output for the receptor configuration of FIG. 3. Sensor receptor attachment resulting in a "standard" reference signal amplitude is shown by the first bar in the sequence. The sensor output signal amplitude is the same for each target in this design. Here, the second receptor group ($R_2$) is bound by its target, producing the signal indicated by the solid bar, with only that target present in the sample. The remaining receptors ($R_1$, $R_3$, $R_4$) remain unbound with zero contribution to the output signal, as indicated by the dotted bars.
Figure 5:
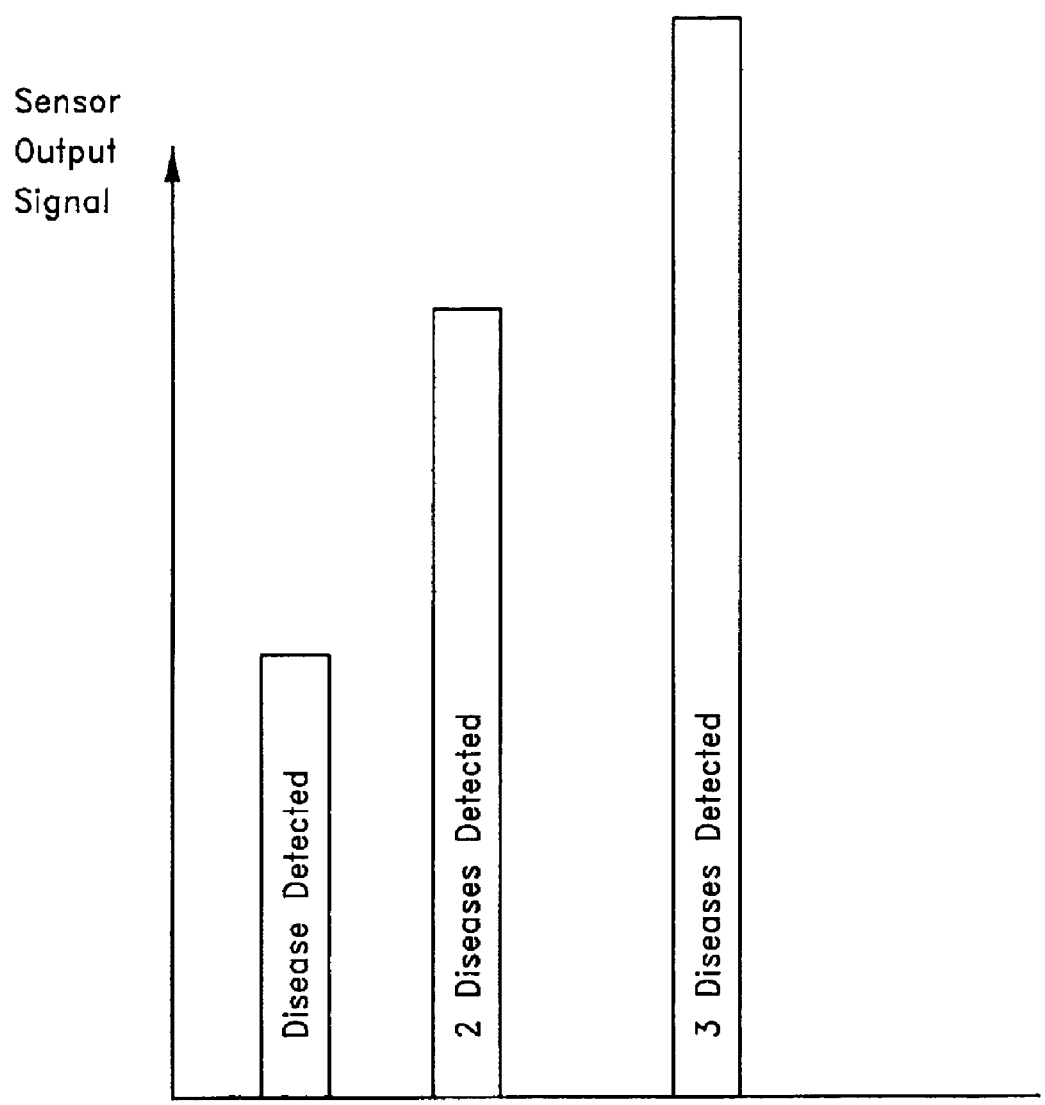
FIG. 5 is a bar graph illustrating signal output from a sensor configured to detect multiple analytes, such as multiple disease indicators. If multiple targets are present for the configuration of FIG. 3, then multiple "standard" amplitudes of approximately equal magnitude will contribute additively to the overall sensor output amplitude. Here, one "unit" of sensor output amplitude $S_D$ indicates a marker for one disease is present, a sensor output signal of $2S_D$ indicates that markers for two diseases are present in the sample, and so on. The sensor thus identifies how many disease related agents are present in the sample.

In another embodiment, the density and absolute number of each type of receptor is not equal (FIG. 3). Preferably, the number of each type of receptor is selected such that the resultant signal for binding of any of the analytes is of approximately the same magnitude, regardless of the identity of the analyte. FIG. 4 illustrates this embodiment, in which binding of each type of analyte to its particular receptors produces an identical signal. The total number of different types of analytes present can then be determined based on the total amplitude of the signal. For example, if two types of analytes are present a signal would be measured that is twice as large as if a single type of analyte was present. In this way, it can be determined how many of the types of analytes being tested for are present in the sample. This example is illustrated in FIG. 5, where each analyte is an indicator of a different disease. Here, a signal of particular amplitude (far left bar) indicates the presence of one type of analyte, corresponding to one disease. A signal that is of twice the magnitude (middle bar) is indicative of two diseases and a signal that is three times larger (far right bar) is indicative of three diseases.

Figure 6:
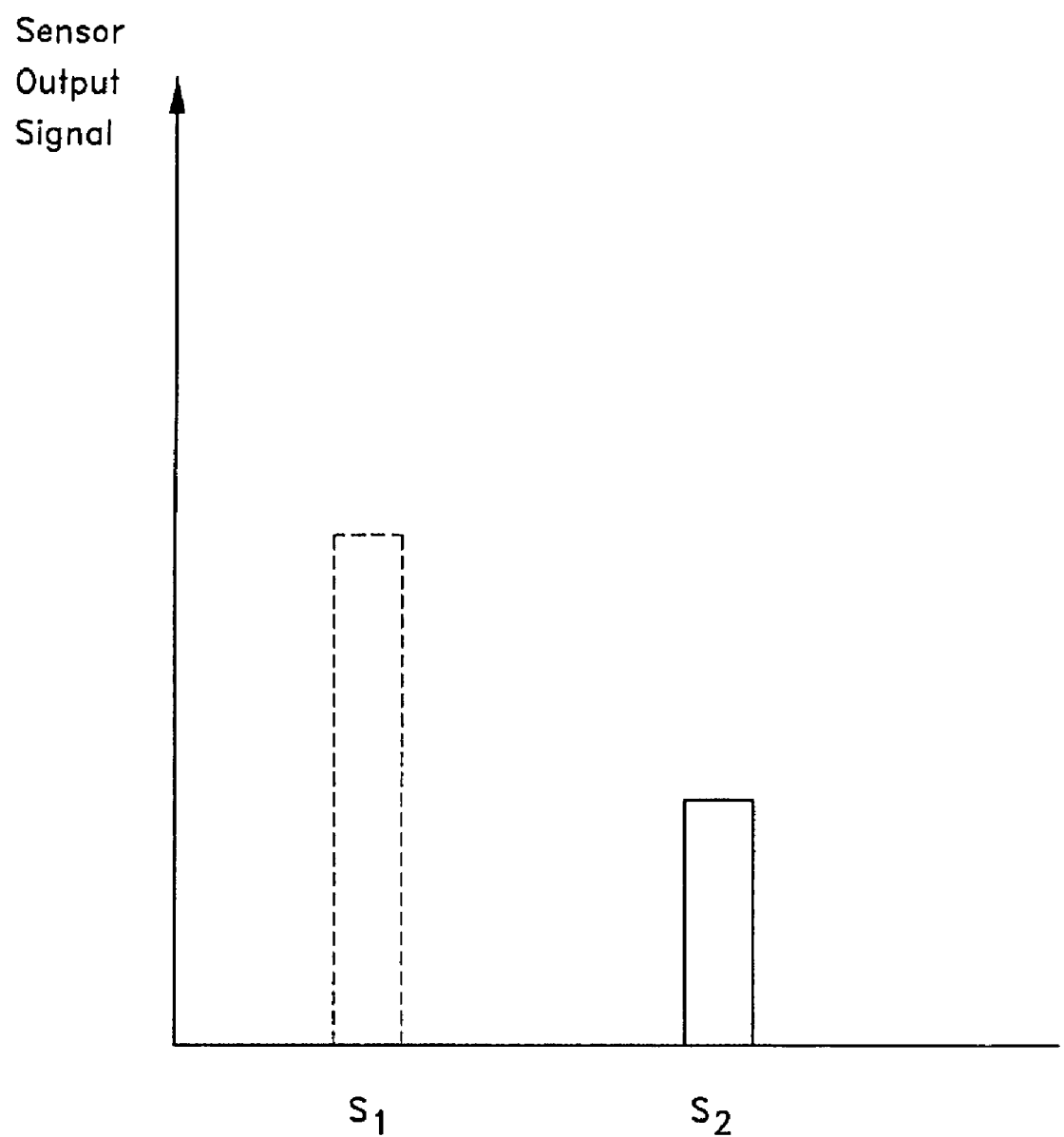
FIG. 6 is a bar graph illustrating weak signal output resulting from a low analyte concentration. In a situation where the concentration of the target analyte is very low, the sensor output signal may be lower than expected ($S_L<S_D$). This allows the sensor to be used to differentiate between concentrations of analyte. For example, where a disease is in the early stages of development, a disease related analyte may be present at a lower concentration than when the disease is at a more advanced stage of development.

In some situations, the amount of analyte present in a sample may not be sufficient to saturate all of the receptors. In this case, as illustrated in FIG. 6, the magnitude of the signal produced by analyte binding may be less (solid line) than the expected signal (broken line). A control sample, comprising a known concentration of analyte, can be used to determine the expected signal for each sensor through routine experimentation.

In addition, a signal that is less than expected may provide additional information about the analyte or about conditions related to the presence of an analyte. For example, if a sensor is used to diagnose the presence of a disease, a smaller than expected signal from a disease related antigen may indicate that the disease is at an early stage. Thus, the sensor can be utilized to determine the stage of a disease in addition to simply diagnosing the disease.

In one embodiment the sensor comprises orthogonal receptors. Here, "orthogonal" refers to two or more receptors that are specific for the same analyte. Preferably, each of the receptors recognizes a different portion of the analyte. For example, the sensor may comprise two or more antibodies to a particular antigen. In this case, each antibody preferably binds to a different epitope on the target antigen. In another specific embodiment two or more different oligonucleotides are provided that bind to the same analyte. For example, two different oligos may bind to different parts of the same DNA or RNA strand. The use of orthogonal receptors provides additional redundancy and and avoids false positives and false negatives that may occur if only a single receptor type is used for a particular analyte.

In some embodiments, the sensor operates as a switch. In these embodiments the number and density of receptors is selected such that the production of any measurable signal corresponds to a particular concentration of an analyte in the sample. In this way the presence of a minimum concentration of analyte in a sample can be determined. This may be useful, for example, in determining if an environmental sample comprises a minimum level of a toxin. In these embodiments, the channel, as described below, is preferably not conducting in the absence of analyte binding to the active region.

Figure 7:
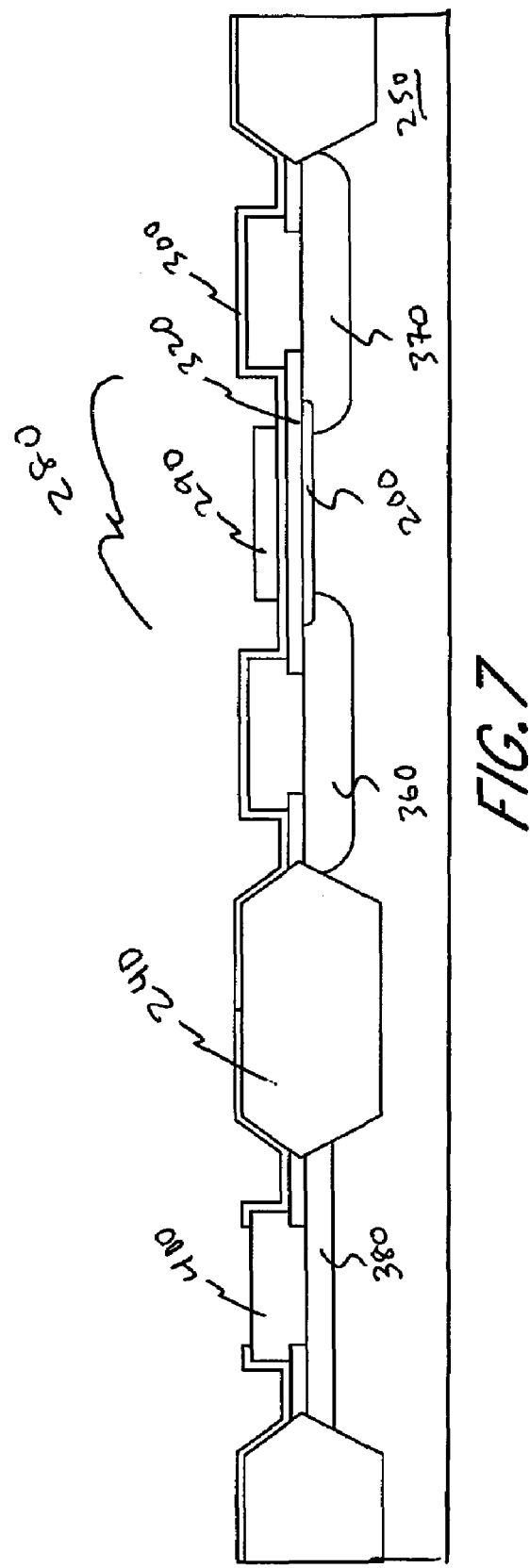
FIG. 7 shows a schematic cross section of a field effect transistor (FET). Here a buried conducting p-channel is formed in an n-Si substrate. The device has voltage tuning of sensor sensitivity. The gate area is represented with a silicon nitride gate dielectric layer covered with a polysilicon gate. The nitride layer also serves as a protective layer over other features in the transistor. Other gate dielectrics may be used. Receptors are attached to the gate.

With reference to FIG. 7, in the preferred embodiments the sensor comprises a field effect transistor (FET) operating in enhancement mode. However, in some embodiments and with some analytes the transistor will operate in depletion mode. Receptors are bound to the gate region of the transistor. In one embodiment the receptors are bound to a gate electrode of poly-Si, as illustrated in FIG. 7. In the illustrated embodiment, a buried conducting p-channel 200 is isolated from an n-substrate 250. The p channel is preferably p+ and conducts in the absence of any input from the top gate. The channel connects a source region 360 and a drain 370. The source and drain are preferably n+.

The gate stack 280 of the illustrated embodiment comprises a polysilicon layer 290 over a gate dielectric, which comprises a layer of silicon nitride 300 over a layer of silicon oxide 320 in the illustrated embodiment. The gate dielectric is preferably between about 100 Å and about 2000 Å, more preferably about 800 Å. In the illustrated embodiment the layer of silicon oxide 320 is about 400 Å thick and the layer of silicon nitride 300 is about 400 Å thick. Other conductive materials besides polysilicon may be used for the top gate electrode. Receptors (not shown) are attached to the gate electrode to form the active region, as described in more detail below. In other embodiments a material that facilitates receptor binding is deposited over the gate electrode and the receptors are attached to this material. In the preferred embodiments, however, the receptors are preferably not attached to an insulator, such as a field oxide, overlying the gate electrode.

Figure 8:
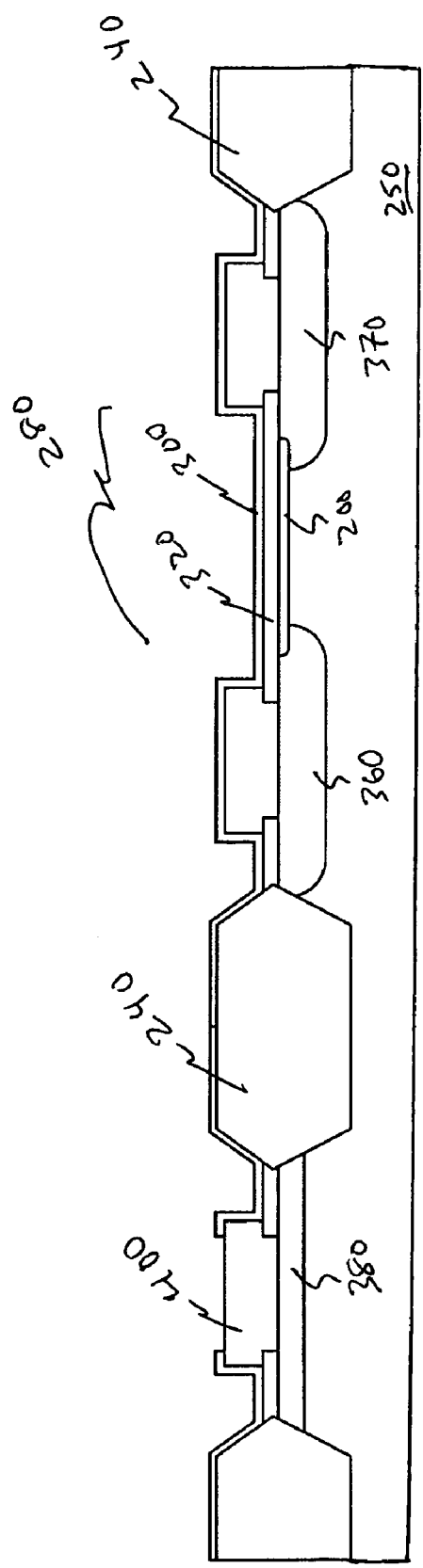
FIG. 8 is a schematic cross section of a field effect transistor (FET) with a naked gate dielectric. Other materials besides poly-Si may be used for the gate, and a gate may be formed in the absence of separate gate materials, as illustrated here. A transistor with just a nitride gate dielectric layer is an attractive embodiment of such a sensor. In this case, receptors are attached to the gate dielectric to form the gate. Additional processing of the gate region may occur depending upon the type of receptors attached and the nature of the analyte of interest.

With reference to FIG. 8, in other embodiments a gate electrode is not present and the receptors are bound to the gate dielectric layer 300 to form the active region. In still other embodiments a material that facilitates receptor binding is deposited over the gate dielectric layer 300 and the receptors are attached to this material.

The gate dielectric also preferably serves as a barrier material that protects the substrate, for example from deleterious interactions with the sample. As illustrated in FIGS. 7 and 8, the gate dielectric extends over and protects the rest of the transistor except at the contact openings. When it functions as a protective layer, the gate dielectric is preferably deposited to a thickness that is able to protect the sensor from a particular sample, as can be readily determined by the skilled artisan.

As the majority of biological analytes are negatively charged, a conducting p-channel is utilized in the preferred embodiments. However, one of skill in the art will recognize that other configurations of the transistor may be utilized depending on the particular circumstances. While a buried conducting p-channel as illustrated operates in enhancement mode for the detection of negatively charged analytes, it would work in depletion mode for the binding of positively charged analytes. Thus, if a particular sensor is configured to signal the presence of a positively charged analyte (i.e., comprises receptors specific for a positively charged analyte), a conducting n-channel can be utilized such that the transistor operates in enhancement mode. In other embodiments the transistor operates in enhancement mode via formation or enhancement of a conducting inversion layer in a channel region upon analyte binding. For example, binding of a negatively charged analyte could form a conducting n-inversion layer in a p+ channel region. In each of these embodiments, the transistor preferably operates in enhancement mode. Thus, manipulation of the bias on a back gate is preferably utilized to enhance sensitivity as described below.

The receptors may be bound directly to the active region over the channel of the transistor. Alternatively, linker molecules may be utilized to attach the receptors to the active region. In still other embodiments, the receptors are synthesized directly on the active region.

Receptors that are specific for the analytes of interest are identified. Typically the receptors have been previously identified as capable of binding the analyte of interest. However, in some embodiments new receptors capable of binding the analyte of interest are identified. For example, antibodies to a particular analyte may be produced by well-known methods. In another example, aptamers that are capable of binding the analyte of interest are identified by screening.

Once a receptor has been identified, a sufficient amount of the receptor is produced or obtained to form the sensors. The receptors are then applied to the active region of the sensor. Typically the active region of each sensor will comprise a single type of receptor. However, in some embodiments, the active region of the sensor will comprise more than one type of receptor. For example, in one embodiment, the active region of a sensor comprises two or more types of receptor that are specific for the same analyte. In other embodiments the active region of a sensor comprises two or more receptors that are specific for different analytes. One of skill in the art can readily determine the appropriate receptor composition for each sensor based on the particular application.

The receptors are attached to the active region of the sensor by methods well-known in the art. The active region preferably comprises a material to which the particular type of receptor can be attached. This material can be chosen by the skilled artisan. In one embodiment the receptors are attached to an active region comprising a polysilicon gate. In another embodiment the active region does not comprise a poly-Si gate and the receptors are attached to a gate dielectric layer, such as a silicon nitride layer. The surface to which the receptors are attached may be modified to facilitate attachment.

The receptors are preferably selectively attached to the active region, such that they are not present on other areas of the sensor. This may be done by masking the other areas (e.g., using conventional resist masks), attaching the receptors to the active area, and removing the mask. In another embodiment, receptors are selectively attached to the active area by controlling the application such that receptors are only provided to the active area. In still further embodiments, the receptors are selectively attached to the active area by selectively activating the active area for receptor binding. An example of such selective activation is described below.

In one embodiment the receptors are selectively attached to the active region via linker molecules. Linker molecules are provided on the surface of the active region of the sensor. The linker molecules are then contacted with the receptors under conditions such that the receptors are bound to the substrate. In some embodiments the linker molecules comprise a protective group that must be removed prior to receptor binding. The protective group may be removed, for example, by exposing the linker molecule to the proper activating conditions, such as light, radiation, electric fields, electric currents or other activators. By controlling the activating conditions, a defined region can be activated. For example, if the protective group is removable by light, a defined region of the substrate comprising the active area may be illuminated (e.g., through a lithography reticle or through a patterned mask on the substrate), thus activating the linker molecules in that area. A receptor may then be contacted with the entire substrate, but will only bind to the activated linker molecules in the defined region. The defined region may be a particular region of the active region of a discrete sensor. In preferred embodiments, however, the defined region comprises the entire active region of one or more discrete sensors. In this way, a particular receptor can be bound to one or more specific sensors in an array, without binding to the remaining sensors. A different discrete area of the substrate may then be activated, such as the active region of a second sensor. A second type of receptor may then be bound to the activated region. The process may be repeated to form an array of sensors, each with a defined specificity, as discussed in more detail below.

In some embodiments, rather than attaching receptors that have been previously synthesized, receptors can be synthesized directly on the active regions of the sensors.

The sample to be analyzed is allowed to contact the active region of the sensor and the output signal is processed and interpreted. Thus, the active region is preferably accessible (e.g., by opening contact vias through an overlying insulating layer) after any higher level metallization.

The areas of the substrate and sensors outside of the active region are preferably covered with a protective material to prevent undesirable interactions with the substrate. The protective material may also serve to prevent binding of charged molecules from the sample outside of the active region. As discussed above, the gate dielectric may serve as a protective material. In other embodiments (not shown) the protective material is an oxide that is deposited over the substrate and patterned to expose the active regions of the sensors. In still other embodiments the protective material is an organic material that can be patterned to expose the active regions. In a particular embodiment the protective material is parylene.

In the preferred embodiments, the sensor output parameter is a voltage, current or resistance change in response to binding of the analyte to one or more of the receptors. The sensor output results from the attached charge and/or a chemical potential change on the active region as a result of analyte binding.

The sensitivity of the sensor can be tuned across a large dynamic range. The sensitivity may be modified by channel doping. In the preferred embodiments, the channel is doped with a dopant type to insure that a buried conducting channel is formed that operates in an enhancement mode. By operating in an enhancement mode, the device typically displays a linear resistance change in response to analyte binding. Thus, the sensor is preferably operated below the pinch off condition. However, in other embodiments analyte binding is determined based on a change in the saturation current. As used herein, "enhancement mode" indicates that binding of the analyte of interest enhances conduction in the channel between the source and the drain.

In embodiments in which the sensor comprises a conducting channel, the sensitivity is preferably enhanced by reverse bias of the channel/substrate PN junction. In these embodiments a back PN junction, or back gate, is used to reduce channel conductance, resulting in an increased proportionate signal upon substrate binding. Preferably, the initial conduction is kept low by manipulating the voltage on this back gate. For example, conductance through an implanted p+ conducting channel is reduced by applying a positive voltage to the back gate, which leads to partial depletion of the channel. In some embodiments, the bias or reverse bias is measured as a sensor parameter.

In addition, the sensitivity can be tuned by selecting a particular size for the active channel area. Sensitivity is increased by making a smaller active region as fewer analyte molecules can be detected by a sensor with a smaller channel area compared to a sensor with a larger active region. Preferably, the active region is made as small as possible to increase sensitivity and to reduce costs, while remaining large enough to accommodate a sufficient number of receptors to produce a desired signal upon analyte binding.

As discussed above, the sensitivity of the sensor may also be controlled by varying the density of receptors on the active region. By increasing the density of receptors, the sensitivity can be increased.

In other embodiments, sensitivity is increased after analyte binding by enhancing the charge of the bound analyte. This is referred to as "charge amplification" and is preferably used where the original target molecule is of low density, has low or no charge, or when the concentration of analyte is low. Charge amplification may be accomplished, for example, by contacting the bound analyte with a secondary charged molecule or complex that specifically binds to the analyte, which in turn is bound to the sensor. The secondary charged molecule may be, for example, a bead, a detergent, a protein, an aptamer, an oligonucleotide or an antibody. In addition, the charge of the secondary molecule may be altered to further increase the signal. In a particular embodiment the secondary charged molecule is an antibody with modified charge. In some embodiments, the secondary charged molecule comprises a bead or other synthetic material that has been modified to have a desired charge. The bead is then derivatized with a molecule that allows the bead to specifically bind the analyte. Upon binding to the analyte, which has bound to the receptor, the secondary charged molecule increases the signal from the sensor proportionate to the charge that it carries. In other embodiments, the secondary charged molecule is introduced to the sample and allowed to bind the analyte, if present, prior to contacting the sensor with the sample.

The ability to enhance the sensitivity of the sensor allows for the identification of small amounts of an analyte of interest in a sample. The sensor can be tuned to detect at least as few as 100 electronic charges. Detection down to 1-10 pM of analyte is achievable.

FIGS. 11 through 25 illustrate the formation of a FET including a buried P+ type channel for use in a sensor. These steps are summarized generally in FIG. 26. However, one of skill in the art will recognize that other conventional methods may be used to form the FET utilized in the sensor.

Figure 11:
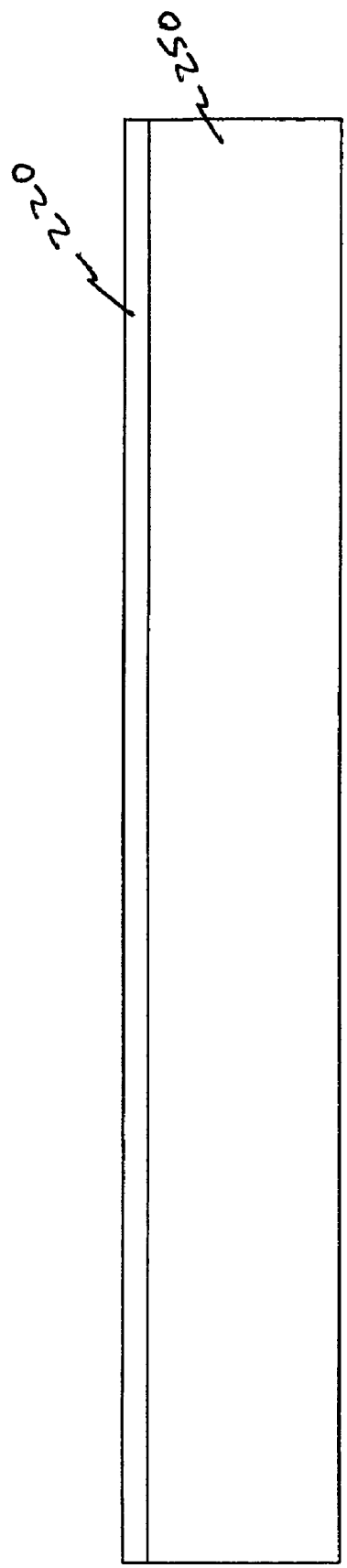
FIGS. 11-25 are a series of cross sections illustrating the formation of a field effect transistor.
Figure 12:
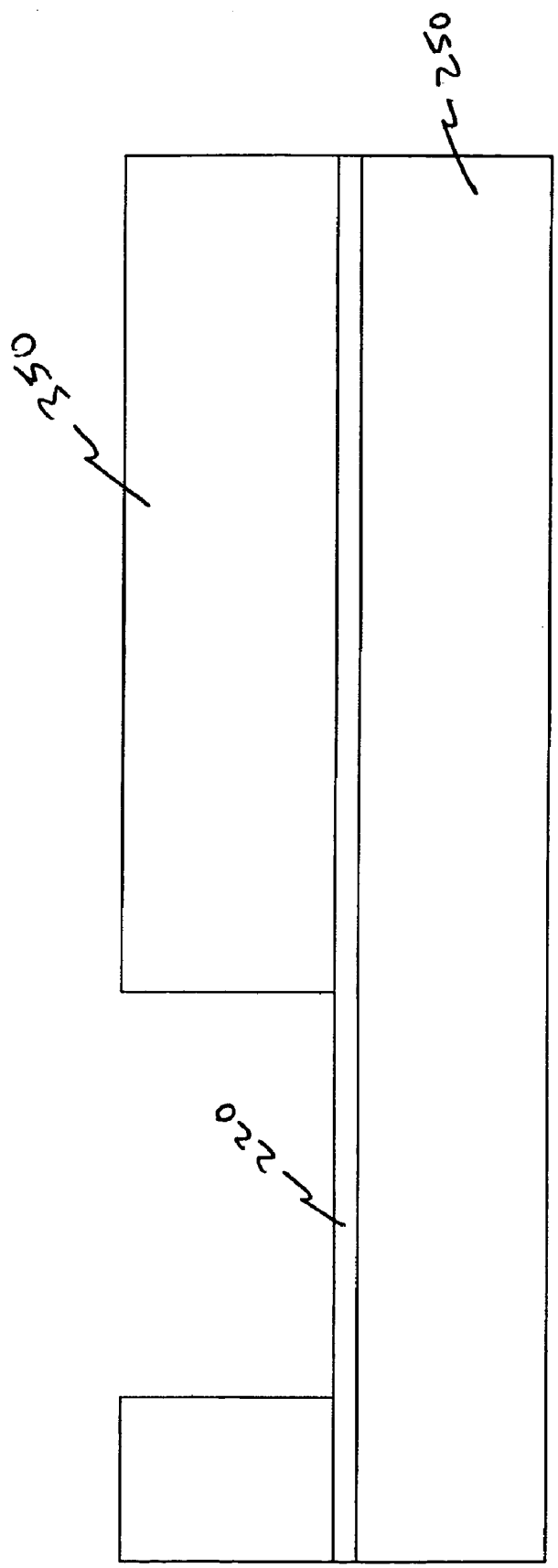
Figure 13:
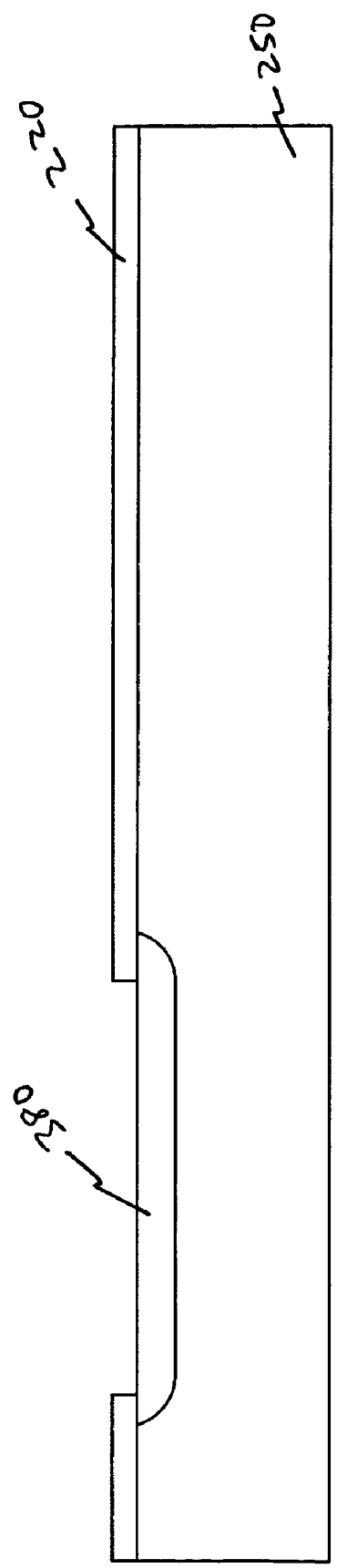
Figure 14:
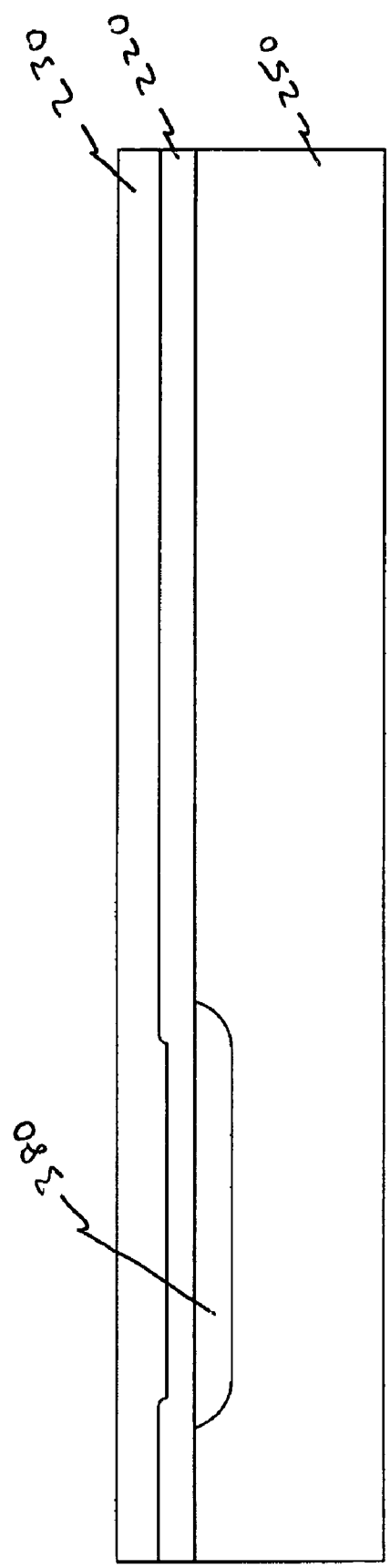
Figure 15:
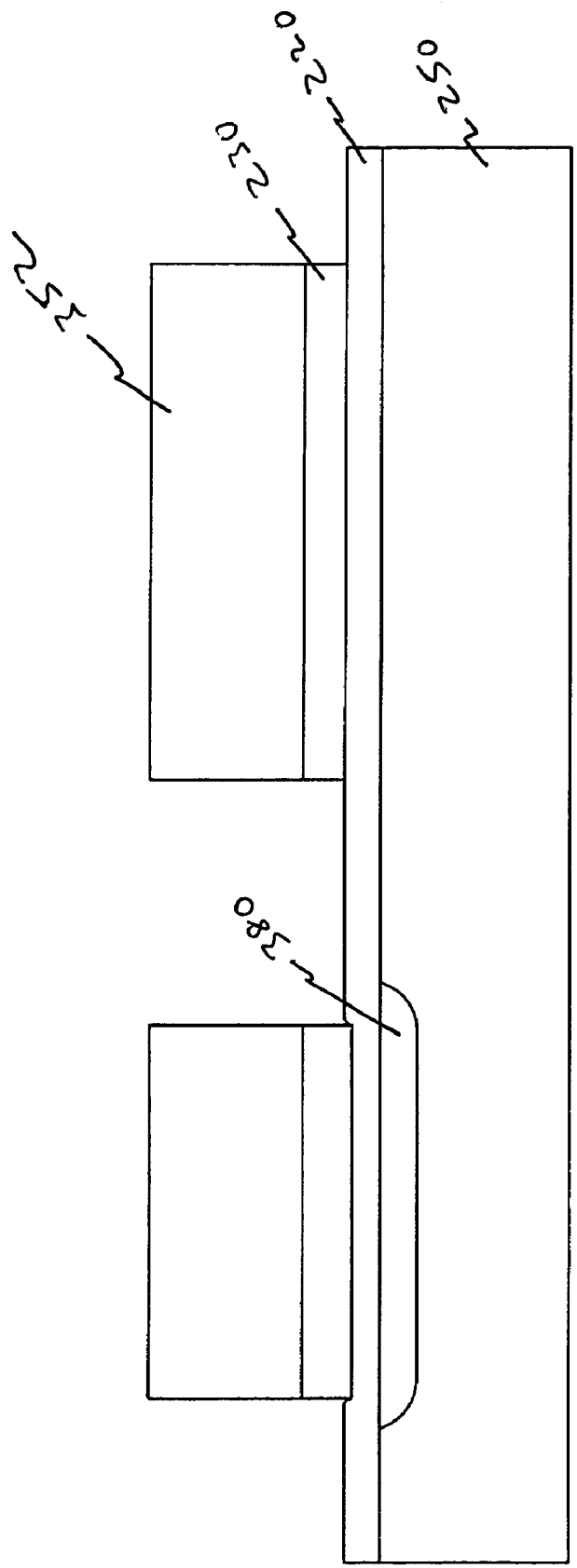
Figure 16:
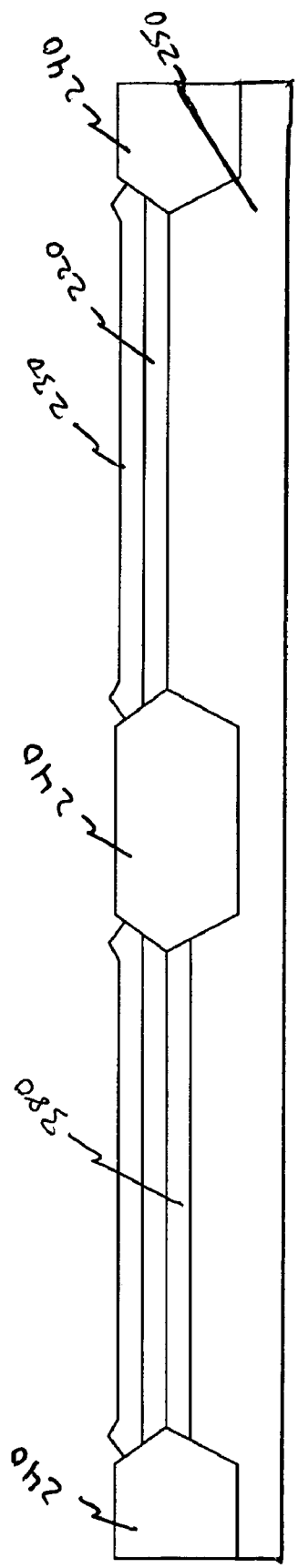
Figure 17:
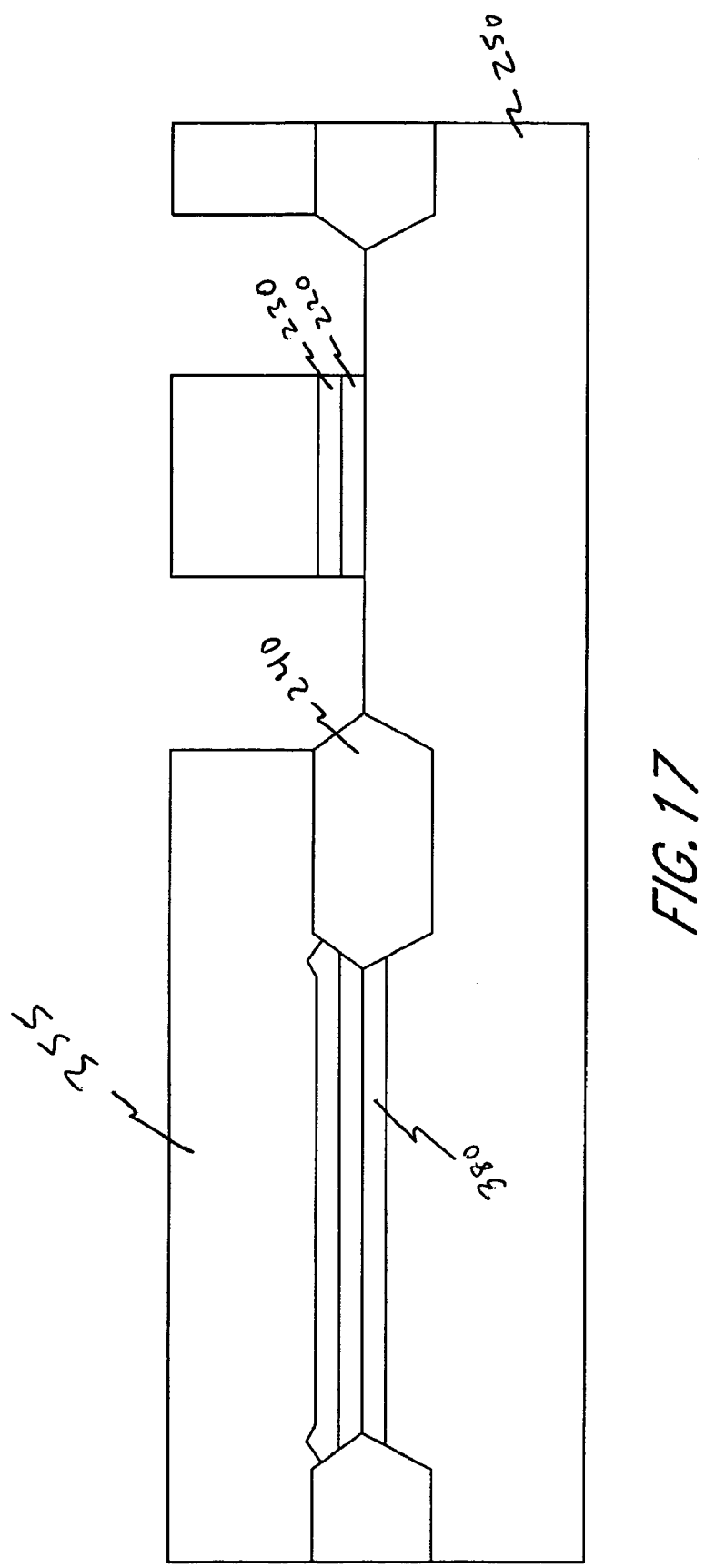
Figure 18:
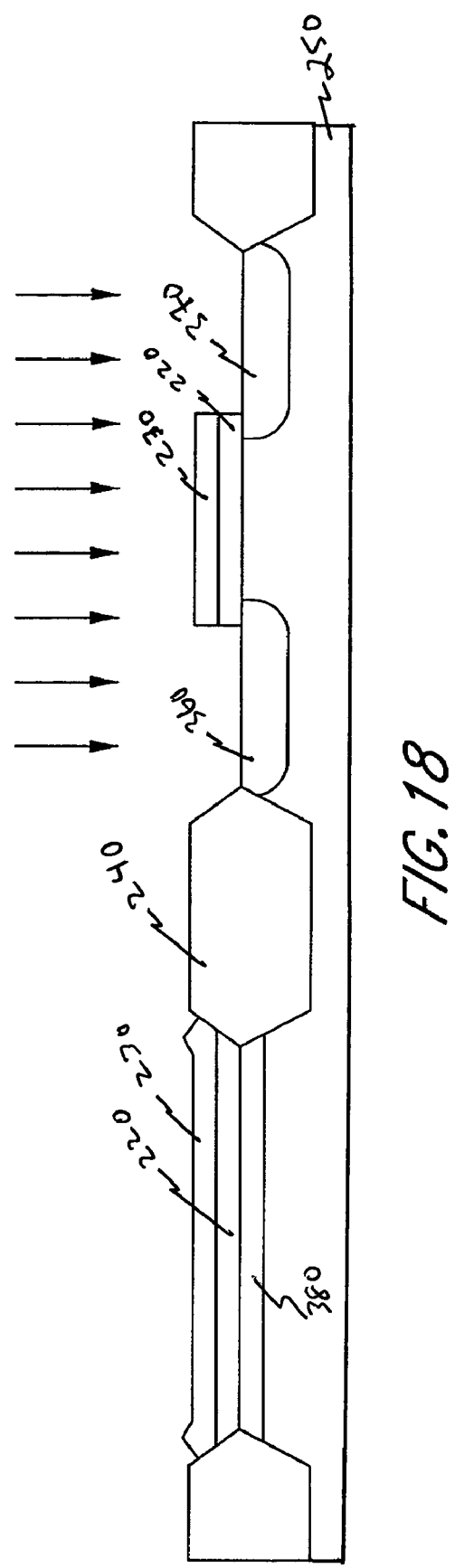
Figure 19:
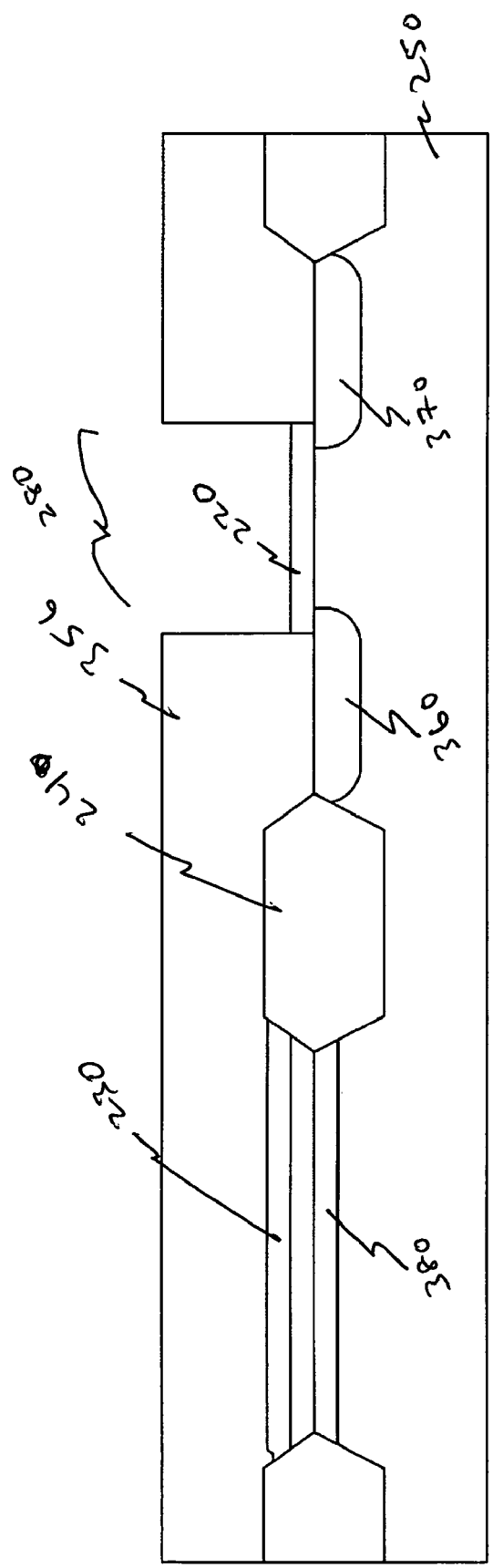
Figure 20:
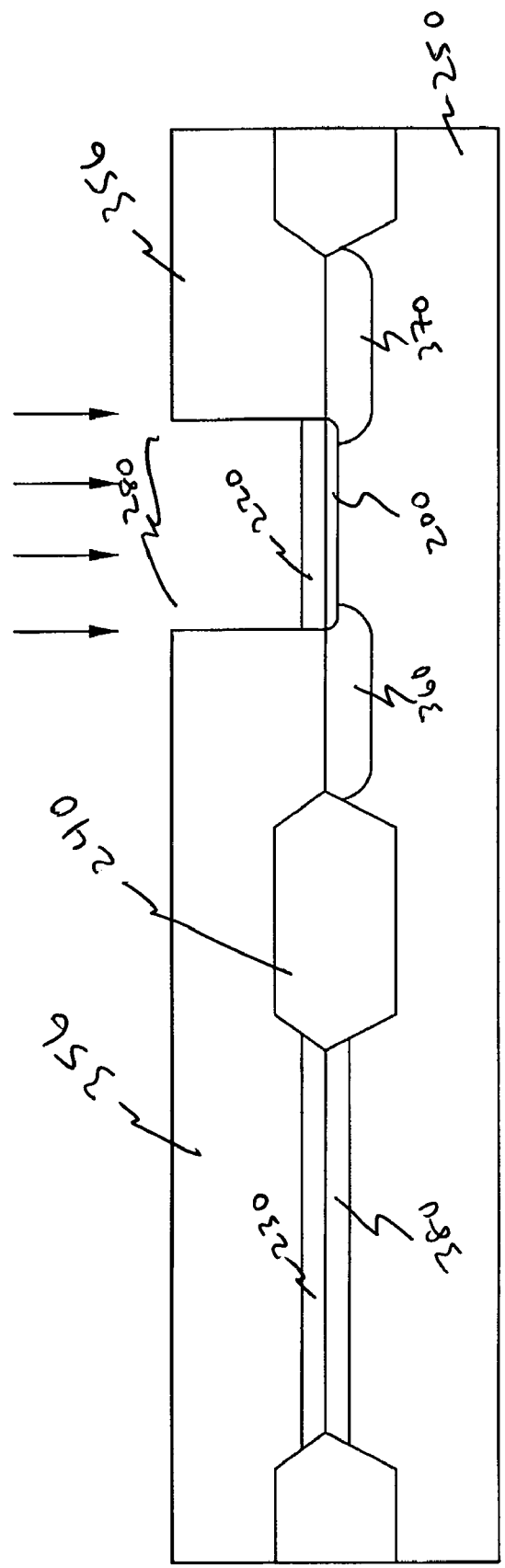
Figure 21:
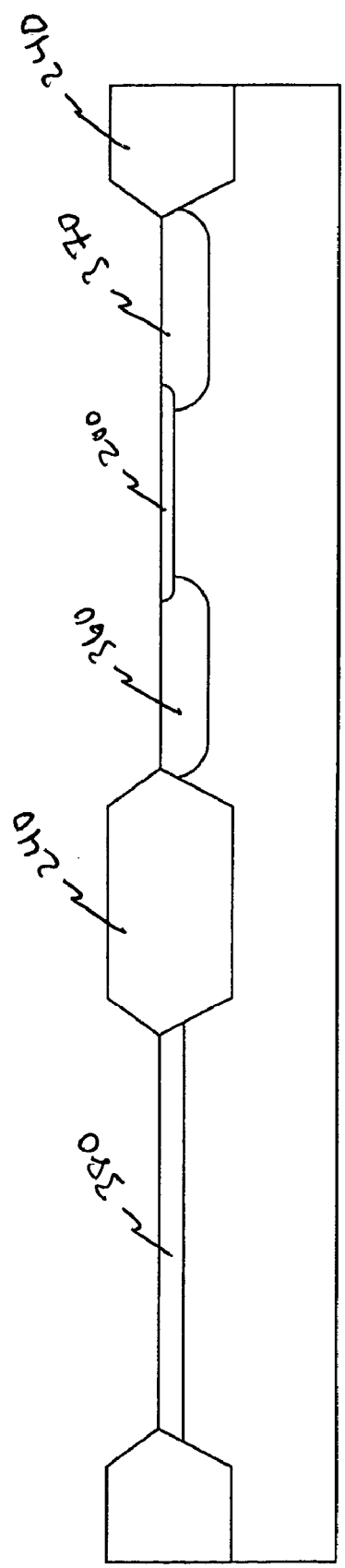
Figure 22:
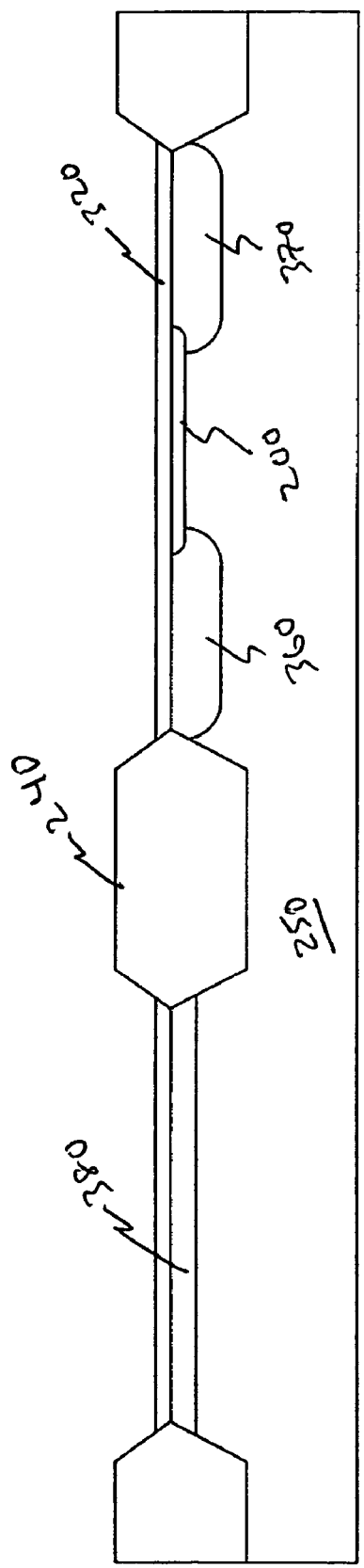
Figure 23:
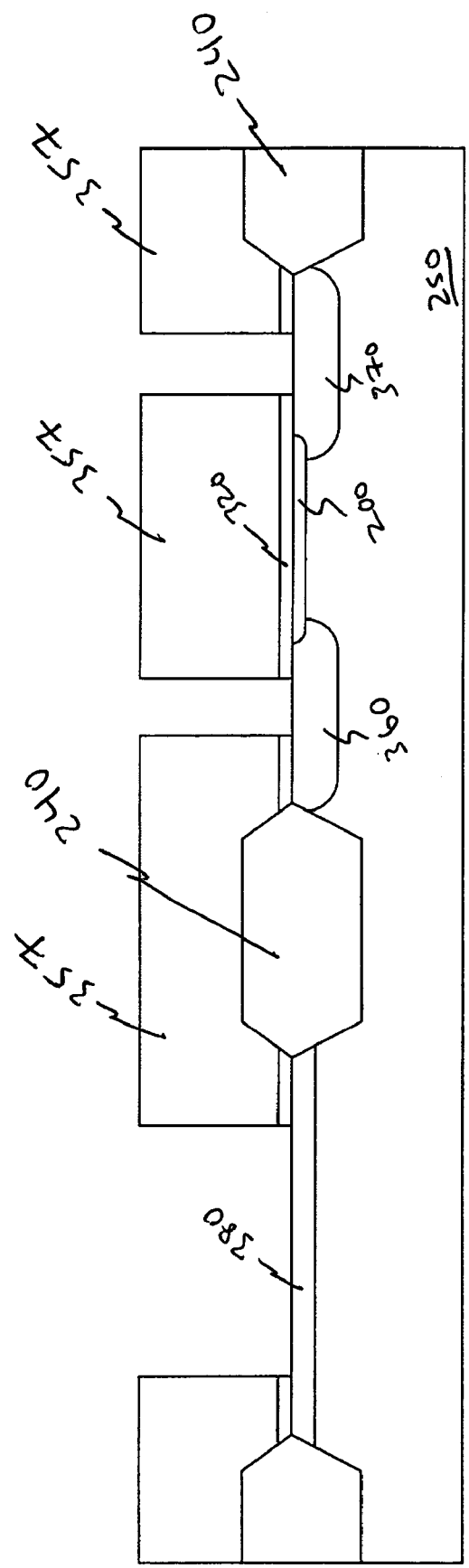
Figure 24:
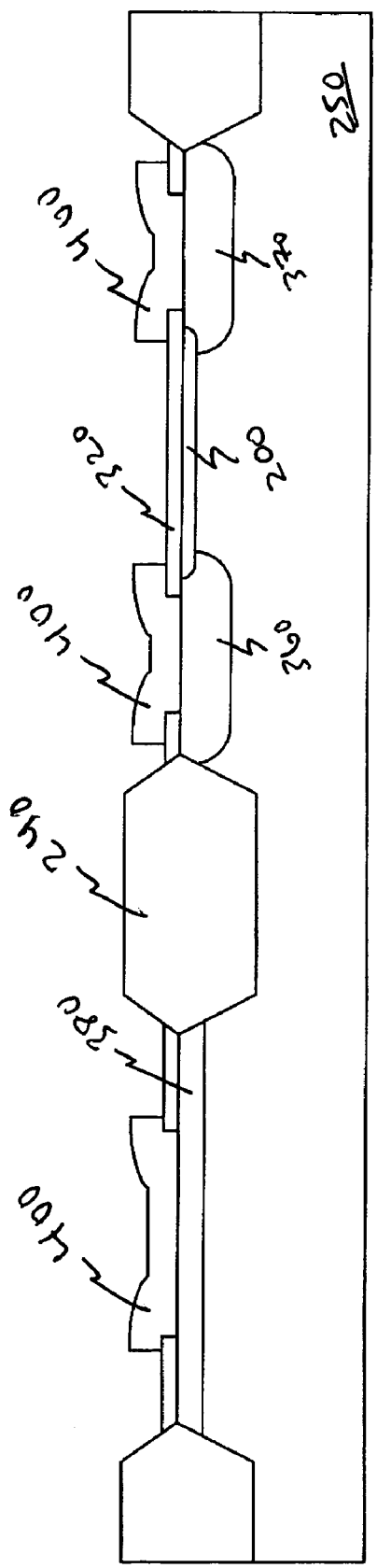
Figure 25:
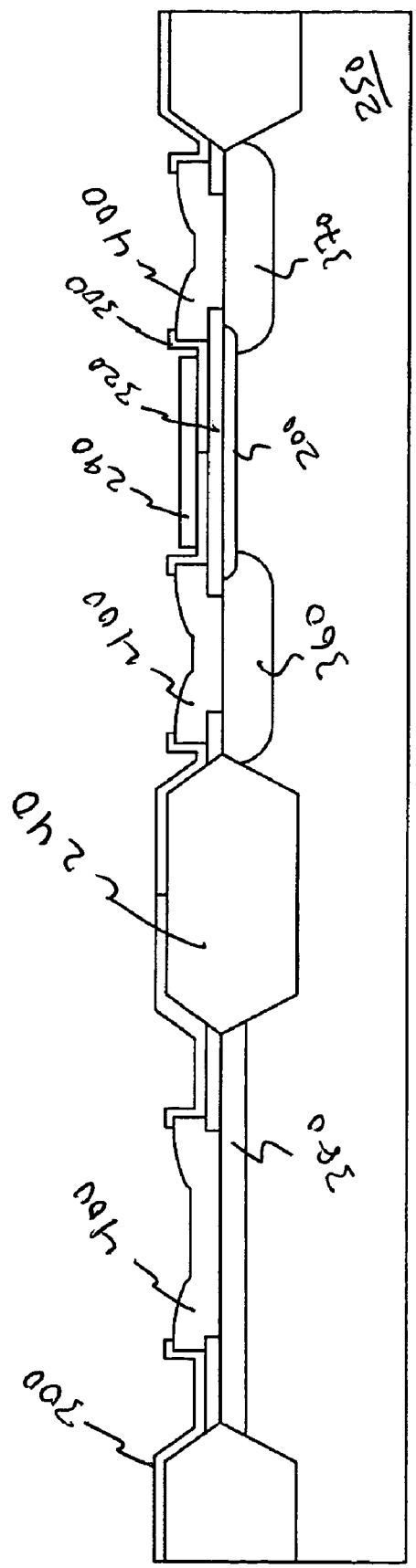
Figure 26:
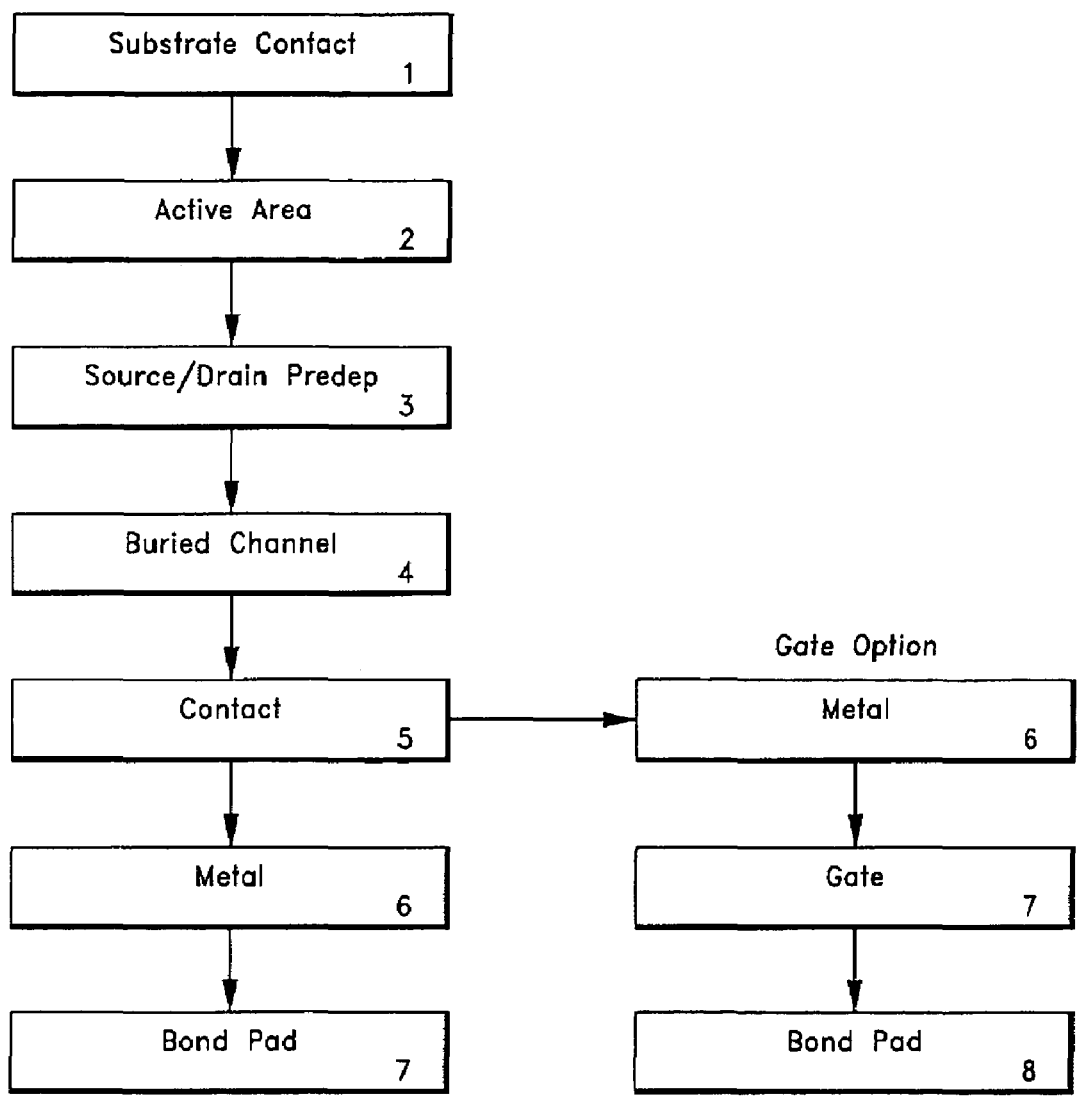
FIG. 26 is a flow chart summarizing the process steps in forming a field effect transistor.

In FIG. 11, an oxide 220 is formed on a p-substrate 250. A photoresist 350 is deposited and patterned to create a substrate contact opening (FIG. 12). A p++ well 380 is formed in the substrate (FIG. 13) and the substrate is covered with a thin film of silicon oxide 220 and silicon nitride 230 (FIG. 14). A layer of photoresist 352 is deposited and patterned and the silicon nitride 230 is selectively removed (FIG. 15) over the areas in which the field oxide 240 is formed (FIG. 16). A second mask 355 is formed and the nitride 230 and oxide 220 are removed over the source and drain windows (FIG. 17) and the source 360 and drain 370 regions are n− doped (down arrows), as illustrated in FIG. 18. The nitride layer 230 is removed over the active region 280 (FIG. 19), a third mask 356 is formed and a buried p+ channel 200 is formed (down arrows; FIG. 20). The remaining oxide 220 is removed to produce the structure illustrated in FIG. 21. A gate oxide 320 is deposited (FIG. 22) and patterned through a fourth mask 357 (FIG. 23). Metal contacts 400 are formed as shown in FIG. 24. Next, sealing layer 300 is deposited and patterned with another mask (not shown) to expose the metal contacts 400 (FIG. 25). Finally, a polysilicon gate 290 is formed over the buried channel 200 as illustrated in FIG. 25. To form a sensor, receptors are subsequently attached to the gate 290 as described above.

It will be understood that other sequences can be employed to arrive at the desired structure.

Arrays

In preferred embodiments, an array of sensors is formed on a single semiconductor substrate and fully integrated with the appropriate addressing and information output circuitry. Memory devices, logic circuitry, readout circuitry, and other appropriate circuitry can be integrated as well, or connected through hybrid means. It is within the skill of one in the art to prepare the circuitry to suit their particular circumstances.

In one aspect, "array" means a predetermined spatial arrangement of sensors present on a substrate. In the preferred embodiment the sensors are formed in a silicon substrate. However, in other embodiments the sensors are formed separately and attached to a solid support. Preferably, the array is addressable. That is, the location and specificity of each sensor is known. However, the specificity of the sensors present at each location is known or may be determined. In one embodiment an addressable location comprises more than one type of sensor. In another aspect, "array" can refer to the spatial arrangement of receptors on the active region of a particular sensor.

The sensors in the array may all be specific for the same analyte. That is, each of the receptors in the array may comprise receptors that are specific for the same analyte. This arrangement may be used, for example, in the case of an array that is designed to detect a single analyte. The presence of multiple receptors with the same specificity provides redundancy and confirmation of the presence of the analyte.

Figure 9:
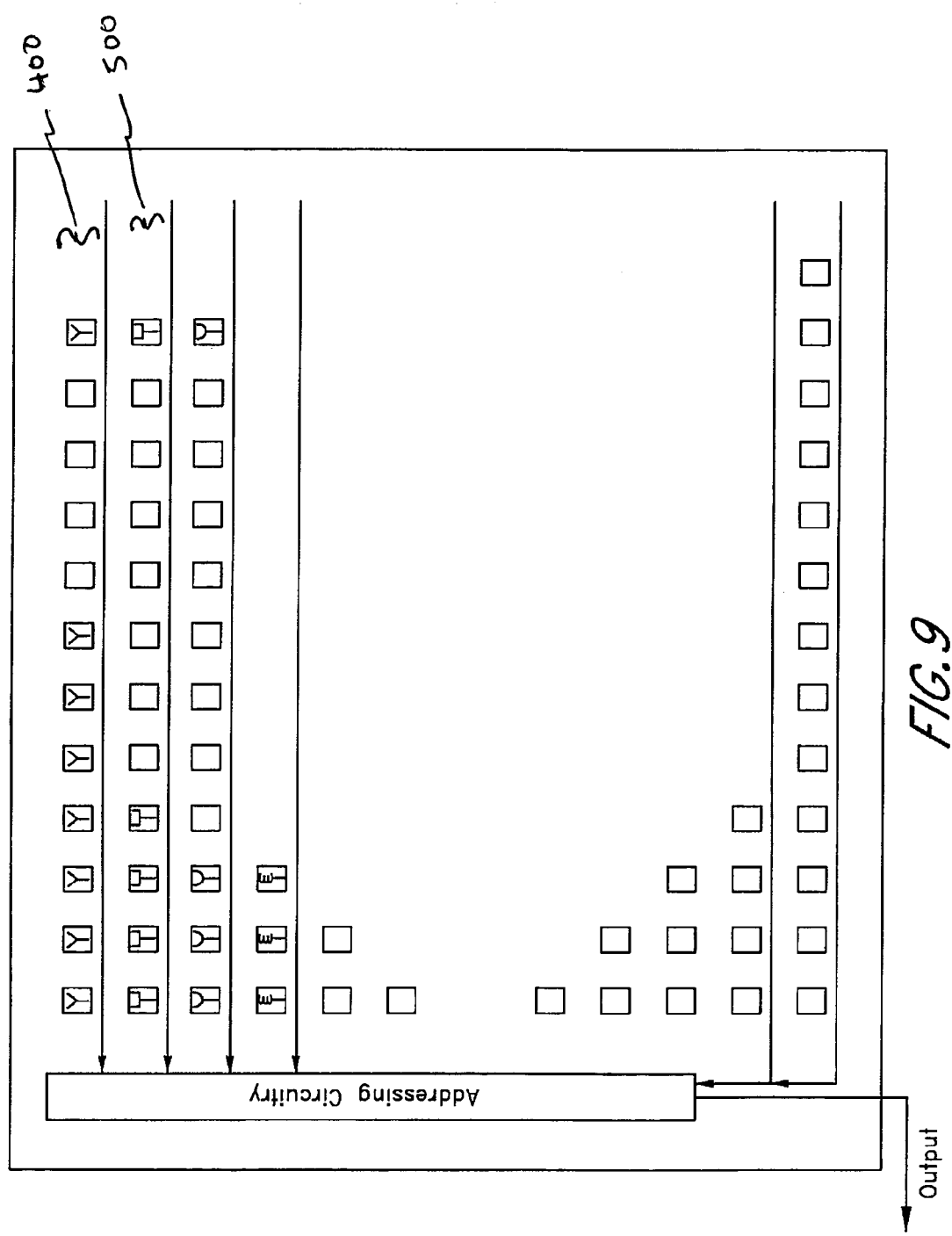
FIG. 9 schematically illustrates a biosensor array. The array comprises rows and columns of biosensors, each sensor in turn comprising receptors for a particular analyte. Redundancy is provided by all sensors in each row having the same type of receptor. Orthogonal receptors to the same target are present in different rows. For large sensor arrays, a single row may have redundancy and orthogonal sensors as well as receptors for multiple different targets. In this example, the sensors are electronic devices integrated with addressing and information output circuitry. Memory devices (not shown) and logic circuitry (not shown) together with readout circuitry (not shown) and other circuitry may be integrated on the same substrate or connected through hybrid means.

In other embodiments, the array comprises sensors that are specific for different analytes. Such an array could be used to detect and/or identify more than one analyte in a sample. An exemplary array is illustrated in FIG. 9. This array comprises multiple rows and columns of sensors, each of which comprises receptors that are specific for a particular analyte. Addressing enables the identification of which transistor is affected, and how, by exposure to the sample.

The array may comprise multiple sensors that are specific for the same analyte. For example, in the array illustrated in FIG. 9 each of the sensors in a particular row comprises the same receptor. This redundancy provides confirmation of the presence of a particular analyte.

In addition, the array may comprise sensors with orthogonal receptors. This is illustrated in FIG. 9, where the sensors in the first row 400 each comprise the same type of receptor, while the sensors in the second row 500 each comprise an orthogonal receptor. Thus, each of the sensors in the first and second row will signal the presence of the same antigen. However, each of the sensors in the second row comprises a receptor that recognizes a different portion of the analyte recognized by the receptors on the sensors in the first row 400. For example, each of the sensors in the first row 400 may comprise a first antibody to an analyte of interest while each of the sensors in the second row 500 comprises a second antibody that differs from the first but that is specific for the same analyte of interest. The presence of orthogonal receptors provides for additional redundancy and avoids false positives or negatives that may be associated with a single receptor type.

In other embodiments the array comprises sensors with receptors that allow for the confirmation of the detection of a particular analyte based on the presence of a second analyte. In these embodiments one or more sensors or groups of sensors in the array are specific for a first analyte, while one or more different sensors or groups of sensors are specific for a second analyte. Here, the second analyte is one that would not be present in the sample unless the first analyte is present. This enhances the redundancy of the test and avoids false positives. For example, if a receptor for a particular infectious agent, such as a virus, is present on one sensor or group of sensors in an array, sensors with receptors to a protein that is produced by a patient in response to infection may also be included. Thus, a sample from a patient could be screened for the presence of the infectious agent and a positive signal could be confirmed by the presence of the associated protein.

An array can comprise a low-density number of addressable locations, e.g. 1 to about 100, medium-density, e.g. about a hundred or more locations, or a high-density number, e.g. a thousand or more. Typically, the array format is a geometrically regular shape, which may facilitate, for example, fabrication, handling, stacking, reagent and sample introduction, detection, and storage. The array may be configured in a row and column format, with regular spacing between each location. Alternatively, the locations may be arranged in groups, randomly, or in any other pattern. In one embodiment an array comprises a plurality of addressable locations configured so that each location is spatially addressable for high-throughput handling.

FIG. 10 illustrates a group of four sensors with different geometric features on a single silicon chip. In particular, the size and shape of the active area 600 varies among the illustrated sensors. An array may constitute an array of either component members of the chip shown, or an array of the group, thereby forming an array of groups of sensors rather than an array of individual sensors. Such sensor group array components may comprise sensor configurations that vary according to the sensor objectives, sensitivity issues, receptor binding issues or other desirable features.

In a preferred embodiment, sensors that are specific for a particular analyte are grouped together on the substrate. For example, all of the sensors that are specific for a particular analyte may be located in a single row on the substrate. Sensors are specific for a particular analyte if each of the sensors comprises receptors that are specific for one particular analyte. The signals from all of the sensors that are specific for a particular analyte may be combined to provide an enhanced signal indicative of the presence of a specific analyte. In other embodiments, the signals are maintained separately.

In other embodiments, the sensors that are specific for a particular analyte are not grouped together.

In a preferred embodiment each of the sensors in the array are connected to addressing circuitry that allows for the collection and analysis of a signal from each sensor. Based on the signal, the presence of one or more analytes of interest is determined. Depending on the arrangement of the array and the design of the sensors, the nature of the analyte and the amount of the analyte may be identified as well. For example, sensors may be included that generate a signal only in the presence of a specific minimum concentration of analyte, as discussed above. The activity of sensors that are tuned to a particular concentration of analyte provide an indication of the minimum concentration of analyte in the sample. If a sensor tuned to a higher minimum concentration is not activated, a maximum analyte concentration can also be determined.

Typically, each sensor in an array comprises one type of receptor. In this case, the number of sensors is at least as great as the number of different types of receptors to be used to identify the analytes of interest, and thus at least as great as the number of analytes to be detected. For example, if the presence of ten analytes is to be detected in a sample, at least ten sensors with receptors specific for those analytes will be present on the substrate. However, if orthogonal receptors are utilized to provide confirmation of binding of a particular analyte, the number of sensors will be higher. The number of sensors will be determined, for example, by the number of analytes to be detected and the physical size of the substrate on which the array is formed.

In one embodiment, at least one sensor comprises more than one type of receptor. Here, the sensor may comprise two or more types of receptor that are specific for the same analyte. Alternatively, the sensor may comprise receptors that are specific for two or more analytes.

Each sensor in the array may be designed to provide the same signal upon binding of an analyte of interest. In another embodiment, the signal provided by each sensor or each type of sensor is variable.

Addressing circuitry enables large numbers of sensors to be included in an array on a single substrate. Thus, the overall size of the array is not limited and will be determined based on a variety of factors, including the number of sensors, the physical size of the sensors, and physical constraints on the size of the substrate. For example, the total size of the substrate and number of sensors may be limited by the available sample size. The total size may also be limited by the circuitry required to link the individual sensors. In one embodiment, the sensors are present on a substrate with an area of about 100 $cm^2$ or less. In another embodiment the sensors are all present on a substrate with an area of about 10 $cm^2$ or less.

For detecting the presence of one or more analytes in a sample, the sample is contacted with the array of sensors and the electrical properties are measured at each sensor. If a change in the electrical properties is identified at any sensor, the analyte that interacts with the receptors on that sensor is identified as being present in the sample.

In another embodiment, the measured signal is a summation of the signal from all of the sensors. In this case, a signal indicates that at least one of the analytes of interest is present in the sample. The type or magnitude of the signal may also be interpreted to determine which analytes are present in the sample.

In one embodiment, the instrumentation is configured to selectively sample for particular sensors or groups of sensors within the array, and thus for particular analytes.

Applications

The analysis of samples for the presence of one or more particular analytes finds uses in a wide range of fields, from medical, basic biological research, pharmaceutical, agricultural, environmental, homeland defense and industrial diagnostics to genomics and proteomics.

The arrays of the invention are useful for diagnostic applications and for use in diagnostic devices. In one embodiment the arrays are used to establish a correlation between the presence of a particular analyte, such as a pathogen or a particular protein, and a disease or a particular stage of a disease. In a further embodiment, once such a correlation between the presence and/or amount of an analyte and a particular disease or a particular stage of a disease has been made, or is known, the arrays of the invention may be used to diagnose a particular disease or a stage of a disease in a tissue of an organism.

Accordingly, in one embodiment, the invention provides a method of diagnosing a disease or disorder in a patient. Multiple diseases can be screened for at the point of care and results provided immediately. One or more analytes that are known to be associated with the disease or disorder from which a patient is believed to be suffering are selected. For example, if a patient is suspected of suffering from a viral infection, the methods of the present invention may be used to identify the presence of one or more proteins that are known to be associated with the infectious agent are selected for identification. For example, a sample from a patient suspected of being infected with HIV may be analyzed for the presence of one or more proteins known to be associated with HIV.

Similarly, the sensors and arrays may be used to evaluate the efficacy of treatment. For example, the presence of one or more analytes known to be associated with a disease or disorder determined in a biological sample from a patient prior to and after treatment. This may help determine the efficacy of particular treatment options.

The sensors may also be used to compare the expression patterns of proteins in different populations of cells or tissues. For example, cells may be subject to different conditions and the expression pattern of particular proteins compared to the protein expression pattern of a control cell or population. For example, the protein expression pattern of a cancer cell may be compared to the protein expression pattern of a control cell or population.

The ability to compare the expression of particular proteins between two cells or two population of cells may be useful in the identification and validation of new potential drug targets, as well as for drug screening. In particular, a protein may be identified which is particularly expressed in diseased cells, but not in normal cells. Such a protein may be a target for drug intervention, such as with inhibitors targeted to such a differentially expressed protein and the effect of different drug candidates on protein expression may be observed.

In a particular embodiment, the arrays may be used to screen environmental samples for the presence of one or more toxic agents or pathogens, such as botulinum toxin, ricin and anthrax, for example in bioterrorism defense or environmental remediation. The arrays allow for the simultaneous detection, identification and quantification of the potential agents in the sample. In addition, the ability to build in redundancy decreases the risk of false reporting, including both false positives and false negatives.

In another particular application, the arrays are used for blood bank screening. If a potential donor has recently contracted a disease or disorder, such as HIV or hepatitis infection, traditional assays may not be able to detect the infection. An array comprising one or more sensors that are specific to a multitude of blood born diseases is prepared. Thus, a single array can be used to screen for multiple diseases. A blood sample is obtained from the potential donor, such as by finger prick, and contacted with the array. A positive signal from the array would indicate the presence of a disease and the donation would be rejected. As the presence of any one of the diseases that are screened would be sufficient to reject the donation, it is not necessary to have an addressable array and costs can be reduced. However, if an addressable array is used, the identity of the disease or disorder can be readily determined and the potential donor can be counseled accordingly.

In an industrial setting a product or intermediate may be analyzed for the presence of a particular compound.

Although the foregoing invention has been described in terms of certain preferred embodiments, other embodiments will be apparent to those of ordinary skill in the art and the skilled artisan will be able to readily adapt the disclosed methods and sensors to a particular use. Additionally, other combinations, omissions, substitutions and modification will be apparent to the skilled artisan, in view of the disclosure herein. Accordingly, the present invention is not intended to be limited by the recitation of the preferred embodiments, but is instead to be defined by reference to the appended claims.

I claim:

1. A sensor for detecting the presence of an analyte in a sample comprising a receptor for the analyte of interest bound to an active region of a field effect transistor (FET), wherein the active region overlies a p+ buried conducting channel connecting a source region and a drain region.

2. The sensor of claim 1, wherein the active region comprises a polysilicon gate.

3. The sensor of claim 1, wherein the active region comprises a gate dielectric layer.

4. The sensor of claim 3, wherein the gate dielectric layer is a silicon nitride layer.

5. The sensor of claim 4, wherein the receptor is bound to the silicon nitride layer.

6. The sensor of claim 1, additionally comprising a back gate.

7. The sensor of claim 6, wherein the sensitivity of the sensor is increased by applying a bias to the back gate.

8. The sensor of claim 7, wherein the receptor is selected from the group consisting of antibodies, antibody fragments, peptides, oligonucleotides, DNA, RNA, aptamers, and organic molecules.

9. The sensor of claim 1, comprising two or more receptors specific for the same analyte.

10. The sensor of claim 1, comprising two or more receptors specific for different analytes.

11. The sensor of claim 10, wherein the density and absolute number of each receptor is not equal, such that the resultant signal for binding of any anolyte of interest is approximately the same magnitude, regardless of the identity of the anolyte.

12. The sensor of claim 10, wherein the number and density of the receptors specific for each analyte are approximately equal.

13. The sensor of claim 1, wherein the sensor operates in enhancement mode upon binding of a negatively charged analyte.

14. The sensor of claim 1, wherein the receptor is bound to the active region via a linker molecule.

15. The sensor of claim 14, wherein the linker molecule further comprises a protective group that prevents binding of the receptor and must be removed by exposure to an activator prior to receptor binding.

16. The sensor of claim 1, wherein conduction of the channel is increased by enhancement of a conducting inversion layer in the channel.

17. The sensor of claim 1, wherein the analyte is selected from the group consisting of toxins, insecticides, polypeptides, nucleic acids, pathogens and drugs.

18. The sensor of claim 1, wherein the number and density of receptors are chosen so that a change in conductance of the channel will occur only if a target analyte is present in the sample at a concentration greater than or equal to a predetermined minimum concentration.

19. The sensor of claim 1, wherein the active region is as small as possible, just large enough to hold enough receptors to generate a measurable signal when the receptors bind to the target analyte, so that the sensitivity of the sensor is increased.

20. A method for identifying the presence of an analyte of interest in a sample comprising: contacting the active region of a sensor with the sample, wherein the sensor comprises one or more receptors for the analyte of interest bound to an active region and wherein the active region overlies a buried p+ conducting channel connecting a source and drain; measuring sensor output; and identifying the presence of the analyte of interest where the sensor output indicates a change in conductance of the channel upon exposing the active region to the sample.

21. The method of claim 20, wherein the sensor output is selected from the group consisting of conductance, voltage and resistance.

22. The method of claim 20, wherein the change in conductance is caused by binding of the analyte to the receptor.

23. The method of claim 22, wherein the analyte is negatively charged.

24. The method of claim 22, wherein binding of the analyte of interest enhances conductance between the source and drain.

25. The method of claim 20, wherein the change in conduction is enhanced by contacting the bound analyte with a secondary charged molecule.

26. The method of claim 25, wherein the secondary charged molecule is an antibody.

27. The method of claim 25, wherein the secondary charged molecule is a bead.

28. The method of claim 20, wherein there are two or more analytes of interest and types of receptors, wherein the density and absolute number of each type of receptor is not equal, such that the resultant signal for binding of any anolyte of interest is approximately the same magnitude, regardless of the identity of the anolyte, and further comprising determining the number of analytes of interest that are present from the sensor output.

29. The method of claim 20, wherein the sensor output indicates a change in conductance only if the target analyte is present in the sample at a concentration greater than or equal to a predetermined minimum concentration.

30. The method of claim 20, wherein there are two or more analytes of interest and receptors specific for each analyte of interest, wherein the number and density of the receptors specific for each analyte are approximately equal, further comprising determining the identity of the analytes present by the amplitude of the sensor output.

31. An array comprising two or more sensors for detecting the presence of an analyte in a sample, each sensor comprising a receptor for a particular analyte of interest bound to an active region of a field effect transistor (FET), wherein the active region overlies a p+ buried conducting channel connecting a source region and a drain region.

32. The array of claim 31, comprising two or more sensors for detecting multiple toxins.

33. The array of claim 31, comprising two or more sensors for detecting multiple disease markers.

34. The array of claim 31, wherein at least two sensors comprise receptors that are specific for the same analyte.

35. The array of claim 31, comprising a first sensor for detecting the presence of a first analyte of interest and a second sensor for detecting the presence of a second analyte of interest.

36. The array of claim 35, wherein the presence of the second analyte of interest provides confirmation of the first analyte of interest.

37. The array of claim 31, comprising at least two orthogonal receptors.

* * * * *

UNITED STATES PATENT AND TRADEMARK OFFICE
CERTIFICATE OF CORRECTION

PATENT NO. : 7,291,496 B2  
APPLICATION NO. : 10/854753  
DATED : November 6, 2007  
INVENTOR(S) : James W. Holm-Kennedy It is certified that error appears in the above-identified patent and that said Letters Patent is hereby corrected as shown below:

Column 6, line 34, delete the second "and".  
Column 7, line 41, "negatively" should read --positively--.  
Claim 11, Column 15, lines 19 and 21, "anolyte", each occurrence, should read --analyte--.  
Claim 28, Column 16, lines 23-24, "anolyte", each occurrence, should read --analyte--.

Signed and Sealed this

Twenty-fourth Day of June, 2008

JON W. DUDAS  
*Director of the United States Patent and Trademark Office*